United States Patent
Coyle

(10) Patent No.: US 6,269,157 B1
(45) Date of Patent: *Jul. 31, 2001

(54) BIDDING FOR TELECOMMUNICATIONS TRAFFIC WITH REQUEST FOR SERVICE

(75) Inventor: William F. Coyle, Summit, NJ (US)

(73) Assignee: Summit Telecom Systems, Inc., Summit, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 09/548,484

(22) Filed: Apr. 13, 2000

Related U.S. Application Data

(63) Continuation-in-part of application No. 09/537,046, filed on Mar. 28, 2000, and a continuation-in-part of application No. 09/467,274, filed on Dec. 20, 1999, and a continuation-in-part of application No. 09/313,144, filed on May 17, 1999, and a continuation-in-part of application No. 09/022,720, filed on Feb. 12, 1998, said application No. 09/022,720, is a continuation-in-part of application No. 09/010,609, filed on Jan. 22, 1998, now Pat. No. 6,005,925, said application No. 09/467,274, is a continuation-in-part of application No. 09/010,609, said application No. 09/010,609, is a continuation of application No. 09/003,170, filed on Jan. 6, 1998, now Pat. No. 5,917,897, and a continuation of application No. 08/804,542, filed on Feb. 24, 1997, said application No. 08/804,542, is a continuation-in-part of application No. 08/553,889, filed on Nov. 6, 1995, now Pat. No. 5,606,602

(60) Provisional application No. 60/143,914, filed on Jul. 14, 1999, and provisional application No. 60/068,888, filed on Dec. 24, 1997.

(51) Int. Cl.$^7$ ............................ H04M 15/00; H04M 7/00
(52) U.S. Cl. ......................... 379/114; 379/220; 379/221
(58) Field of Search ...................................... 379/220, 221, 379/112, 113, 114, 115, 121, 124, 219, 201, 229, 230; 370/352, 238

(56) References Cited

U.S. PATENT DOCUMENTS 4,122,308  10/1978  Weinberger .
4,410,765  * 10/1983  Hestad et al. ......................... 379/112

(List continued on next page.)

FOREIGN PATENT DOCUMENTS 92306779.7  7/1992  (EP) .
07236011    5/1995  (EP) .
07162525    6/1995  (EP) .

OTHER PUBLICATIONS

ABC–A State–of–The–Art Private Networking Solution L'Onde Electrique 71 (1991) Sep./Oct., No. 5, Paris, FR.
PCT/IL96/00124 Mashinsky, A. Apr. 17, 1997.

Primary Examiner—Curtis Kuntz
Assistant Examiner—Rexford Barnie
(74) Attorney, Agent, or Firm—Allen N. Friedman; McCarter & English LLP

(57) ABSTRACT

Because of technological and regulatory changes, telecommunication service is becoming more of a commodity, with competition between service providers for traffic. The herein disclosed invention stimulates this competition and facilitates a service provider's and a consumer's ability to make economic choices between competing telecommunication carriers. In this method and system, telecommunication switches route calls in accordance with economic incentives (e.g., least cost routing) resulting from a bidding process between participating telecommunication carriers (Carriers), administered by a bidding service provider through operation of a central processor, at computer referred to as a bidding moderator (Moderator). The technology required to facilitate forward delivery transactions, in which a buyer and seller agree to the terms of a transaction today but schedule actual delivery for a future time, would be helpful to end users, resellers and Carriers. The Moderator can facilitate such transactions by processing requests for end users or resellers (as buyers) for telecommunications services to be delivered by Carriers in the future. In order to provide the Moderator with sufficient information to process such a request, the buyer enters the information describing the request on a software-derived template and transmits such information to the Moderator.

55 Claims, 27 Drawing Sheets

U.S. PATENT DOCUMENTS

| | | | |
|---|---|---|---|
| 4,486,626 | | 12/1984 | Kohler . |
| 4,567,359 | | 1/1986 | Lockwood . |
| 4,577,066 | * | 3/1986 | Bimonte et al. .................... 379/112 |
| 4,580,011 | | 4/1986 | Glaser . |
| 4,585,904 | * | 4/1986 | Mincone et al. ................... 379/112 |
| 4,640,986 | | 2/1987 | Yotsutani . |
| 4,706,275 | * | 11/1987 | Kamil ................................ 379/112 |
| 4,751,728 | * | 6/1988 | Treat .................................. 379/114 |
| 4,782,485 | | 11/1988 | Gollub . |
| 4,791,665 | | 12/1988 | Bogart et al. . |
| 4,831,649 | * | 5/1989 | Mejane .............................. 379/112 |
| 4,866,763 | | 9/1989 | Cooper et al. . |
| 4,924,510 | | 5/1990 | Van-Ban Le . |
| 4,972,464 | * | 11/1990 | Webb et al. ....................... 379/112 |
| 5,008,929 | | 4/1991 | Olsen et al. . |
| 5,042,064 | | 8/1991 | Chung . |
| 5,150,405 | | 9/1992 | Lee . |
| 5,163,042 | * | 11/1992 | Ochiai ............................... 379/112 |
| 5,173,933 | * | 12/1992 | Jabs et al. ......................... 379/112 |
| 5,185,785 | | 2/1993 | Funk . |
| 5,216,591 | | 6/1993 | Nemirovsky . |
| 5,247,571 | | 9/1993 | Kay . |
| 5,249,221 | | 9/1993 | Ketring . |
| 5,289,536 | * | 2/1994 | Hokari .............................. 379/112 |
| 5,337,352 | | 8/1994 | Kobayashi . |
| 5,400,395 | * | 3/1995 | Berenato ........................... 379/112 |
| 5,425,084 | * | 6/1995 | Brinskele .......................... 379/112 |
| 5,425,085 | * | 6/1995 | Weinberger et al. .............. 379/112 |
| 5,425,090 | | 6/1995 | Orriss . |
| 5,436,957 | | 7/1995 | McConnell . |
| 5,473,630 | * | 12/1995 | Penzias et al. .................... 379/112 |
| 5,508,999 | | 4/1996 | Cox, Jr. . |
| 5,515,425 | * | 5/1996 | Penzias et al. .................... 379/112 |
| 5,519,769 | * | 5/1996 | Weinberger et al. .............. 379/112 |
| 5,524,142 | | 6/1996 | Lewis et al. . |
| 5,532,939 | * | 7/1996 | Psinakis et al. ................... 379/112 |
| 5,553,124 | * | 9/1996 | Brinskele .......................... 379/112 |
| 5,606,602 | * | 2/1997 | Johnson et al. ................... 379/115 |
| 5,638,433 | | 6/1997 | Bubien, Jr. . |
| 5,652,841 | * | 7/1997 | Nemirovsky et al. ............ 379/112 |
| 5,781,620 | * | 7/1998 | Montgomery et al. ........... 379/115 |
| 5,790,642 | * | 8/1998 | Taylor et al. ..................... 379/112 |
| 5,802,502 | * | 9/1998 | Gell et al. ......................... 379/114 |
| 5,878,121 | * | 3/1999 | Nakanishi ......................... 379/112 |
| 5,878,122 | * | 3/1999 | White et al. ...................... 379/112 |
| 6,005,925 | * | 12/1999 | Johnson et al. ................... 379/112 |
| 6,005,926 | * | 12/1999 | Mashinsky ........................ 379/114 |

\* cited by examiner

BIDDING FOR TELECOMMUNICATIONS TRAFFIC WITH REQUEST FOR SERVICE

RELATED APPLICATIONS

This application depends for priority on Provisional Application Ser. No. 60/143,914, filed Jul. 14, 1999 and is a Continuation-in-Part of application Ser. No. 09/537,046 filed Mar. 28, 2000, application Ser. No. 09/467,274, filed Dec. 20, 1999; application Ser. No. 09/313,114, filed May 17, 1999; and application Ser. No. 09/022,720, filed Feb. 12, 1998. Applications Ser. No. 09/022,720 and 09/467,274 are Continuations-in-Part of application Ser. No. 09/010,609, filed Jan. 22, 1998 which issued on Dec. 21, 1999 as U.S. Pat. No. 6,005,925. Application Ser. No. 09/010,609 is a Continuation-in-Part of application Ser. No. 08/804,542, filed Feb. 24, 1997 and application Ser. No. 09/003,170 filed Jan. 6, 1998, now U.S. Pat. No. 5,917,897, and depends for priority on Provisional application Ser. No. 60/068,888 filed Dec. 24, 1997. Application Ser. No. 08/804,542 is a Continuation-in-Part of application Ser. No. 08/553,889, Filed Nov. 6, 1995, now U.S. Pat. No. 5,606,602, issued Feb. 25, 1997.

GOVERNMENT FUNDED RESEARCH

Not Applicable

BACKGROUND OF THE INVENTION

1. Field of the Invention

The invention is in the field of telecommunication network control.

2. Description of the Background Art

Many locally managed telecommunication systems, such as PBXs, employ "least cost routing" software to reduce telecommunication costs. The system's manager arranges with more than one interexchange carrier to carry the system's traffic from the local exchange to which it is connected to other exchanges. The manager keeps track of each carrier's charges and populates the routing table in the "least cost routing" software. The charges may be the regularly tariffed charges of the subscriber's primary carrier or contracted charges offered by an alternate carrier for a bulk discount or for discounting traffic during a specific time period during the day. The "least cost routing" software will examine each call attempt and automatically decide which carrier is the best economic choice for that call. If the call attempt fails, the software usually defaults the call attempt to the subscriber's primary carrier.

Telecommunication carriers regularly enter into wholesale contractual arrangements with other carriers to use part or all of such other carriers' telecommunications networks, for example, to complete calls to geographic regions the first carrier does not serve or to provide additional capacity on routes, or portions of routes, for which the first carrier may have little or no available capacity on its own network facilities at that time.

Recently a great deal of competition has developed between telecommunication carriers. This has been stimulated by both regulatory and technological changes. As telecommunication becomes more of a commodity it would be of great benefit to consumers to stimulate this competition and facilitate both a carrier's and a consumer's ability to make economic choices between telecommunication carriers.

SUMMARY OF THE INVENTION

Provision of telecommunication services is presently dominated by fixed contractual relationships, between service providers on a wholesale basis and between users and service providers on a retail basis. However, because of technological and regulatory changes, telecommunication service is becoming more of a commodity, with competition between service providers for traffic. The herein disclosed invention stimulates this competition and facilitates a service provider's and a consumer's ability to make economic choices between competing telecommunication carriers. In this method and system, telecommunication switches route calls in accordance with economic incentives (e.g., least cost routing) resulting from a bidding process between participating telecommunication carriers (Carriers), administered by a bidding service provider through operation of a central processor, a computer referred to as a bidding moderator (Moderator).

In this arrangement, each of the Carriers transmits to the Moderator the rate it is willing to charge (or other economic incentive it is willing to offer) for service between two specific switching points on one or more telecommunications networks, at some particular time. This "bid" rate may be for a route or a route segment. For purposes of differentiating in this document between a route and route segment, a "route" is service from the "originating switching point," i.e., the switching point on a telecommunications network that serves as the most immediate switching interface between the calling party and that telecommunications network (e.g., a local exchange switch or equivalent local switching node, whether hardware or software-defined, providing access to that network), to the "terminating switching point," i.e., the switching point on a telecommunications network (which may, but need not be, owned or operated by the same carrier who owns or operates the originating switching point) that serves as the most immediate switching interface between the called party and that telecommunications network (e.g., a local exchange switch or equivalent local switching node, whether hardware or software-defined, providing access to that network). A "route segment" is any and all of the following: (i) service from an originating switching point on a telecommunications network to an "intermediate switching point" on the same or different telecommunications networks, such "intermediate switching points" being all switching points on one or more telecommunications networks that do not serve as the most immediate switching interface between the calling party and a telecommunications network or the most immediate switching interface between the called party and a telecommunications network, but do serve as switching points elsewhere in the telecommunications network or networks over which a call attempt may be routed (e.g., a tandem switch, a high-speed router or some other hardware or software-defined intermediate switching node on a telecommunications network); (ii) service from one intermediate switching point on a telecommunications network to another intermediate switching point on the same or different telecommunications networks; and (iii) service from an intermediate switching point on a telecommunications network to a terminating switching point on the same or different telecommunications networks. An originating switching point and terminating switching point may also be referred to in this application as an "originating switch" or a "terminating switch", respectively, when describing the network switching infrastructure of a local telecommunications service provider.

Carriers may submit bids for routes or route segments to the Moderator for different types of telecommunications networks (e.g., circuit-switched, frame relay, asynchronous transfer mode, packet data networks such as the Internet, etc., whether using electronic, photonic or other technology) and for different classes or qualities of telecommunications service provided by such networks (e.g., transmission of voice, data, video, etc.). Access to such telecommunications networks or facilities by end users or by other telecommunications carriers or service providers may be, for example, via the public switched telephone network, dedicated facilities, private lines, wireless facilities, fiber optic facilities, coaxial cable, electric utility power lines, Ethernet or other local area network (LAN), metropolitan area network (MAN) or wide area network (WAN) connections.

The bid rate may be lower than that Carrier's established rate for any of several reasons (e.g., the Carrier has excess capacity on a particular route or route segment at that time). The Carrier may, for example, also decide for capacity or competitive reasons to place the same bid (i) on all traffic having the same originating switching point (e.g., an NPA-NXX) independent of terminating switching point or independent of which intermediate switching points such traffic may pass through, or (ii) on all traffic having the same terminating switching point independent of originating switching point or independent of which intermediate switching points such traffic may pass through. The Carrier may change its bids as often as it likes during the day as traffic patterns change. The Moderator collects this bid information from all the Carriers, sorts it among switching points, and may further process this bid information, for example, to select Carriers for particular routes or route segments or for individual call attempts. This carrier selection information may include, for example, a prioritization of the Carrier selection in accordance with Carriers' bids for each route or route segment or the designation of a selected Carrier and, perhaps, a default Carrier. The Moderator then transmits selected portions of this information to each appropriate subscribing switch location and to participating Carriers' network management centers. Each subscribing switching point (a "Subscriber") gets the rate information and/or carrier selection information from the Moderator for all "point-to-point" routes or route segments for service from the Subscriber to all other switching points. The Moderator provides each Carrier with bid information from other Carriers for at least a portion of all "point-to-point" routes or route segments for which any Carrier has submitted a bid (e.g., any originating NPA-NXX to any other NPA-NXX or to any intermediate switching point on the public switched telephone network in the world). A route or route segment may be entirely contained within a single local exchange area.

From the list of all Carriers providing bid information to the Moderator, the Moderator or the Subscriber can select those Carriers to which it wants traffic routed and can change that selection at any time. The Subscriber downloads the bid information and/or carrier selection information of those selected Carriers into the routing tables in its switch. After each new bid is submitted by a Carrier and is processed by the Moderator, the rate and/or carrier selection information will be distributed to the relevant Subscribers and rate information will be distributed to other Carriers. The Carriers receiving the information will have the opportunity thereafter to submit a lower or higher bid for any point-to-point route or route segment on which they wish, respectively, to stimulate or discourage additional traffic.

Similarly, the Moderator could offer a different class of service directly to end users who are calling parties. As part of such a service, Carriers would provide an economic incentive for all such end users in a given local exchange area (e.g., an NPA-NXX or group of NPA-NXXs served by a switch) to originate calls terminating anywhere (e.g., by means of a low rate or stated discount). In that case the Moderator would broadcast (e.g., by wired data link or wireless transmission) rate information or carrier selection information generated by the Moderator to an interface unit at each end user location. The information may be displayed for evaluation by the end user or processed within the interface unit, with direction from the end user, and all outgoing calls routed to the selected Carrier. If the Carrier information is displayed for the end user, the user can choose a Carrier for a call attempt and key in the selected Carrier's Carrier identification code before the desired destination address (e.g., telephone number). If the information is processed automatically within an interface unit in the line between the user's terminal equipment and the local exchange switch, the interface unit can, for example, automatically insert the appropriate Carrier identifier before outgoing telephone numbers.

Through this bidding process, Carriers can compete for traffic on selected routes or route segments, or compete for traffic originating from selected points, in telecommunication networks. They can also manage their network traffic by adjusting their bids from time to time, depending on network traffic information or other network information. And users as well as other telecommunication service providers (who may, for example, wish to use the bidding process to obtain a lower rate for resale to customers) can easily make economic choices.

In order not to require each end user or reseller to establish a billing arrangement with each Carrier taking part in the bidding process, a central billing arrangement is advantageous. Such billing arrangements can be implemented with bill preparation performed by the Moderator, by an independent billing service provider, by the end user or reseller (e.g., a local exchange carrier owning or operating a subscribing switch) or by the selected Carrier.

The technology required to facilitate forward delivery transactions, in which a buyer and seller agree to the terms of a transaction today, for example, but schedule actual delivery for a future time, would be helpful to end users, resellers and Carriers. The Moderator can facilitate such transactions by processing requests for end users or resellers (as buyers) for future telecommunications services to be delivered by Carriers.

In order to provide the Moderator with sufficient information to process such a request, the buyer will enter the information describing the request on a software-derived template and transmit such information to the Moderator.

Some subscribing switches (referred to in this application as Auction Switches) may be provisioned to treat every call attempt presented to them as a call attempt which is to be routed to the low-bidding Carrier (e.g., a switching point dedicated for use only by calling parties or resellers who are customers of the Moderator's auction service). In some other cases, the Subscriber function can be incorporated in a more capable switching point (e.g., a local exchange switch or equivalent local switching node) handling call attempts from calling parties who are customers of the Moderator's auction service and from other calling parties who are not. For example, in some telecommunications networks, such as packet data networks (e.g., networks used to carry IP packets, ATM cells, frame relay frames, etc.), each call attempt can include data fields in addition to an unique calling party identifier (e.g., a packet origination address) and a called party (or destination) address. One or more of the switches through which a call attempt passes can process some or all of the information in these additional data fields and route the call attempt in accordance with such information. For example, call attempts requiring a higher quality of service than others (e.g., IP packets that are part of a video transmission) may include in each packet such an additional data field with a high-priority service type indicator or code. One or more of the switches through which these packets pass will process that data field indicator and then route such packets to less congested transmission paths (with fewer delays and/or packet loss) than those paths over which lower priority traffic might travel. Some or all of the information in these additional data fields processed by the switch can indicate to the switch that the call attempt is to be routed in accordance with the Moderator's auction service.

DETAILED DESCRIPTION OF THE INVENTION

Figure 1:
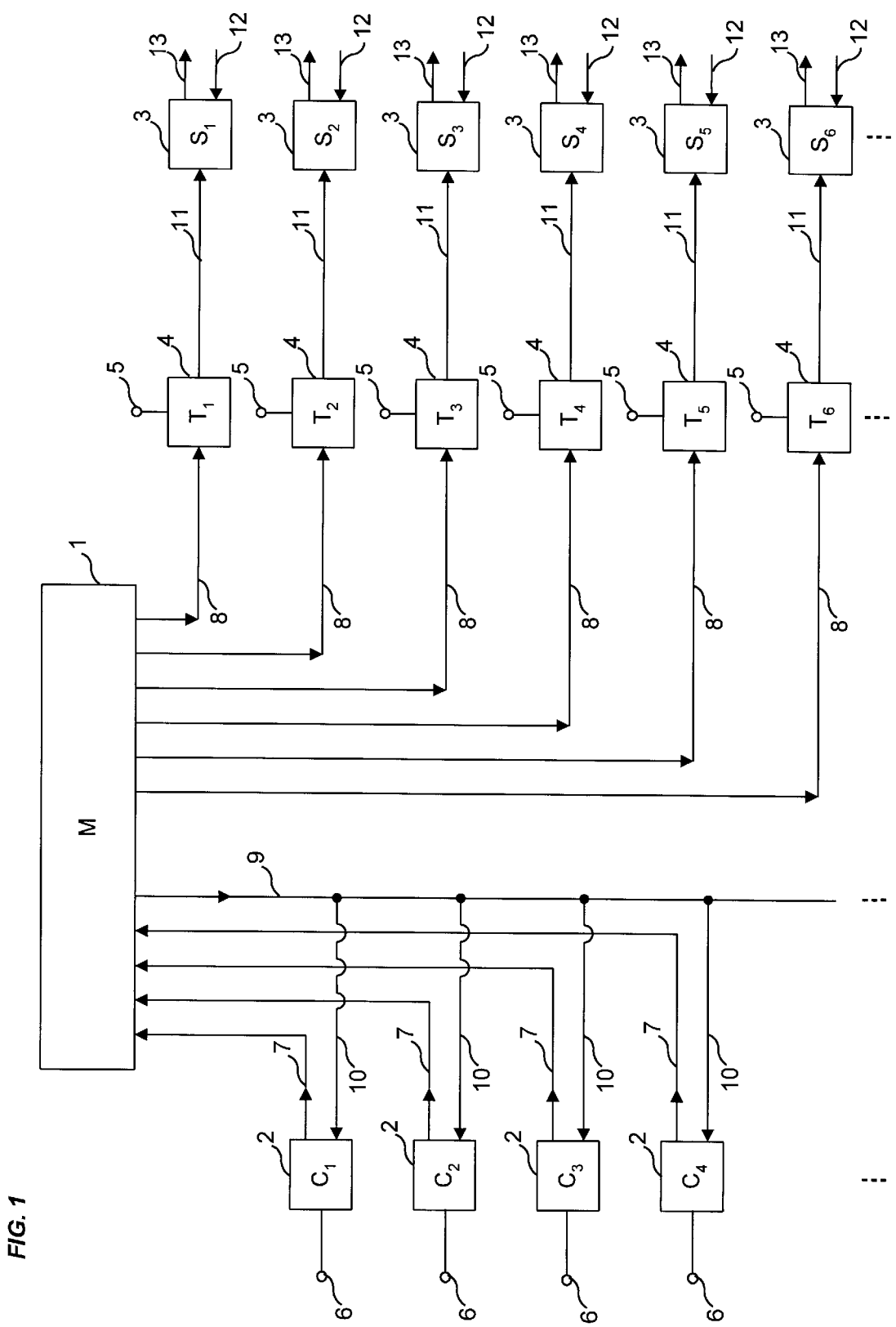
FIG. 1 is a schematic view of an exemplary system of the invention showing dedicated communications lines from each Carrier to the Moderator, from the Moderator to each of the subscribing switches, and a common data link from the Moderator to each of the Carriers.

FIG. 1 shows an exemplary system for carrying out the herein disclosed bidding process for telecommunication services, in which a Moderator 1 collects, processes and disseminates bidding information. The Moderator 1 includes a computer with a processor and memory, together with input and output devices to communicate with the Carriers' network management computers 2, which are the source of the bidding information, and the subscribing switches 3 (Subscribers), which are the ultimate users of the bidding information.

The Carriers are, primarily, Carriers that carry telecommunication traffic between switching points (e.g., originating and terminating switching points such as local exchange switches or equivalent local switching nodes) on telecommunications networks. By means of the FIG. 1 system, for example, the Carriers bid for traffic from subscribing switches 3, associated with a switching point on a telecommunications network, to other switching points on the same or different telecommunications networks. Some circumstances may result in the bidding process controlling carriage of a call attempt over a route or route segments within a single local exchange area. A local exchange area is, typically, the geographic region served by a local exchange switch (or equivalent local switching node). The Carriers transmit their bids from their network management computers 2 over data links 7, which may be either analog (using modems) or digital. However, the information is usually transmitted in digital form for input into the Moderator 1. Each Carrier has a network administrator who enters network management instructions into each network management computer 2 through input port 6 by means, for example, of a keyboard or a data link from a remote site or local computer.

Carriers may submit bids for routes or route segments to the Moderator for different types of telecommunications networks (e.g., circuit-switched, frame relay, asynchronous transfer mode, packet data networks such as the Internet, etc. whether using electronic, photonic or other technology) and for different classes or qualities of telecommunications service provided by such networks (e.g., transmission of voice, data, video, etc.). Access to such telecommunications networks by end users or by other telecommunications carriers or service providers may be, for example, via the public switched telephone network, dedicated facilities, private lines, wireless facilities, fiber optic facilities, coaxial cable, electric utility power lines, Ethernet or other local area network (LAN), metropolitan area network (MAN) or wide area network (WAN) connections.

The Moderator 1 receives the bids, processes them in its processor, sorts them, for example, by originating point or to produce carrier selection data, and enters both into a database in its memory by means of the data buses and registers internal to a computer. The carrier selection data, applicable to each Subscriber 3, are transmitted to such switch 3, perhaps by way of a computer 4 adjunct to the switch 3 over a data link 8. The data link 8 is illustrated as a dedicated transmission facility between the Moderator 1 and each switch 3. However, any other transmission technology offering a selective way to transmit data from the Moderator 1 to the switch may be used. (A "transmission facility" is a telecommunication path or channel. It may be, for example, a wired link, a radio channel in a wireless system, or a time slot in a digitally multiplexed optical transmission system). The data inputs and outputs of the Moderator 1, the network management computers 2, the adjunct computers 4, and the switches 3 are implemented by such devices as interfaces, registers and modems that are well known in the art.

Figure 6:
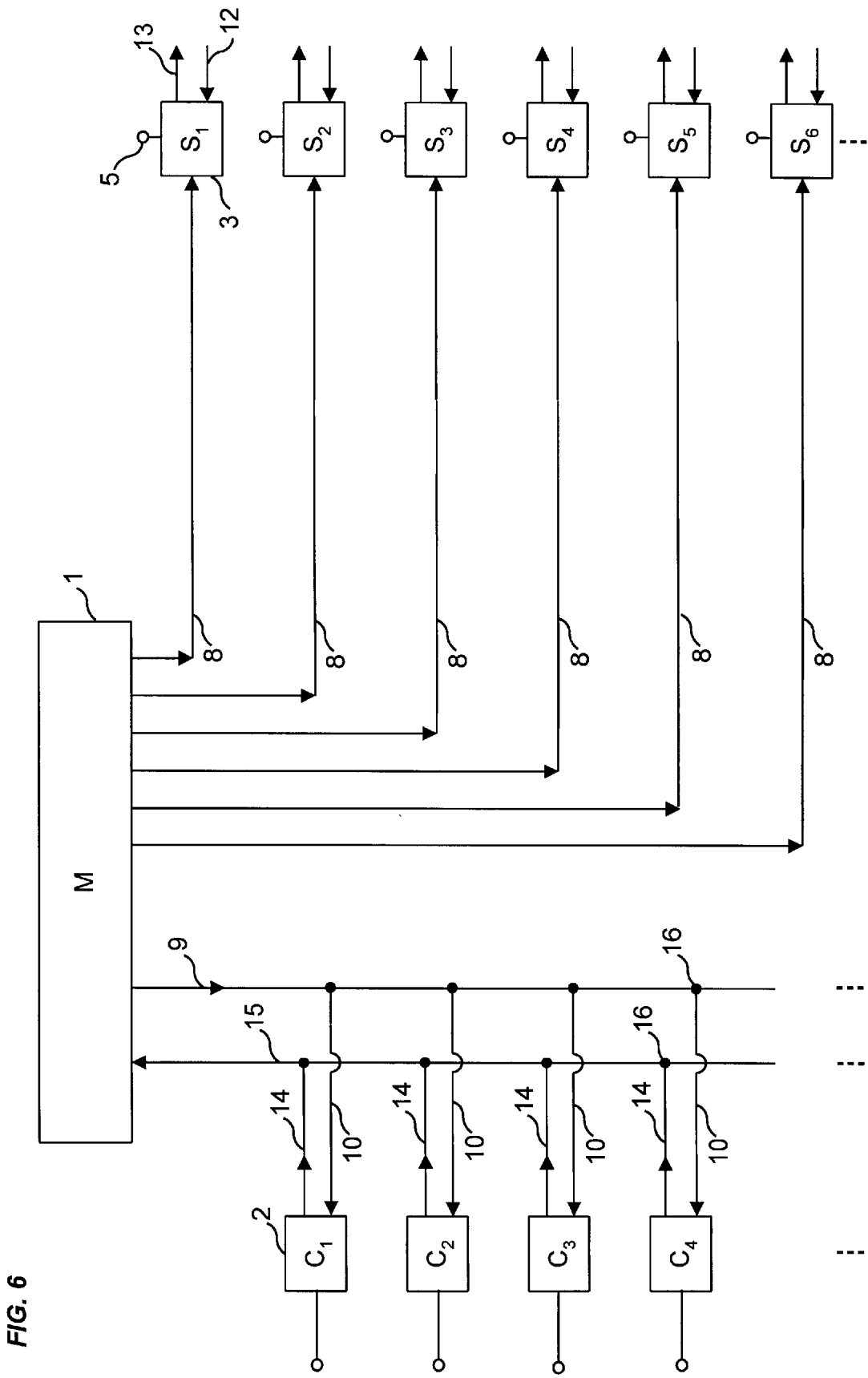
FIG. 6 is a schematic view of an exemplary system of the invention in which the Moderator transmits data directly to the switches.

As illustrated in FIG. 6, the Moderator 1 processes the bids to prioritize them for each route or route segment, producing derivative data, including carrier selection data. This data can reflect, for example, designation of a selected Carrier and alternate Carriers, based on the Carriers' bids for each route or route segment. The Moderator 1 transmits the applicable bids and/or the derivative data to the switch 3. The Moderator 1 or the switch 3 can also designate a default Carrier in the event a call attempt cannot be completed via a Carrier selected by the bidding process. The switch 3 can also be equipped to override the Moderator's selection in accordance with decision rules from the switch administrator 5 (e.g., if the default Carrier designated for the switch 3 charges a rate lower than the lowest bidding Carrier).

An adjunct computer is known in the art to be a computer, closely associated with a switch, that provides the switch's operating software additional data or operating logic to provide the switch with additional operational capability. In the herein disclosed architecture, while primary processing of the bid data to produce carrier selection data is performed in the Moderator, as illustrated in FIG. 1, the adjunct computer 4 can be employed to enter the carrier selection data received from the Moderator 1 into a database in its memory and receive, through input port 5, decision rules from the switch administrator. Software in the adjunct computer's processor can then access the data in memory and apply the decision rules to the carrier selection data, producing the data required to populate the routing tables of the routing software in the switch 3. The adjunct computer 4 communicates with the switch 3 over a digital data link or data bus 11. If the switch 3 has enough processing capacity, the function of the adjunct computer 4 may be incorporated in the switch's processor and memory, the function being implemented in the processor by appropriate software. In this case the switch must also provide input ports to receive transmission link 8 and input 5 from the switch administrator. Each switch 3 receives call attempts over incoming lines 12. Each call attempt includes routing data identifying the call's destination. The switch's routing software then selects the Carrier to which the call attempt shall be routed over outgoing line 13.

Figure 7:
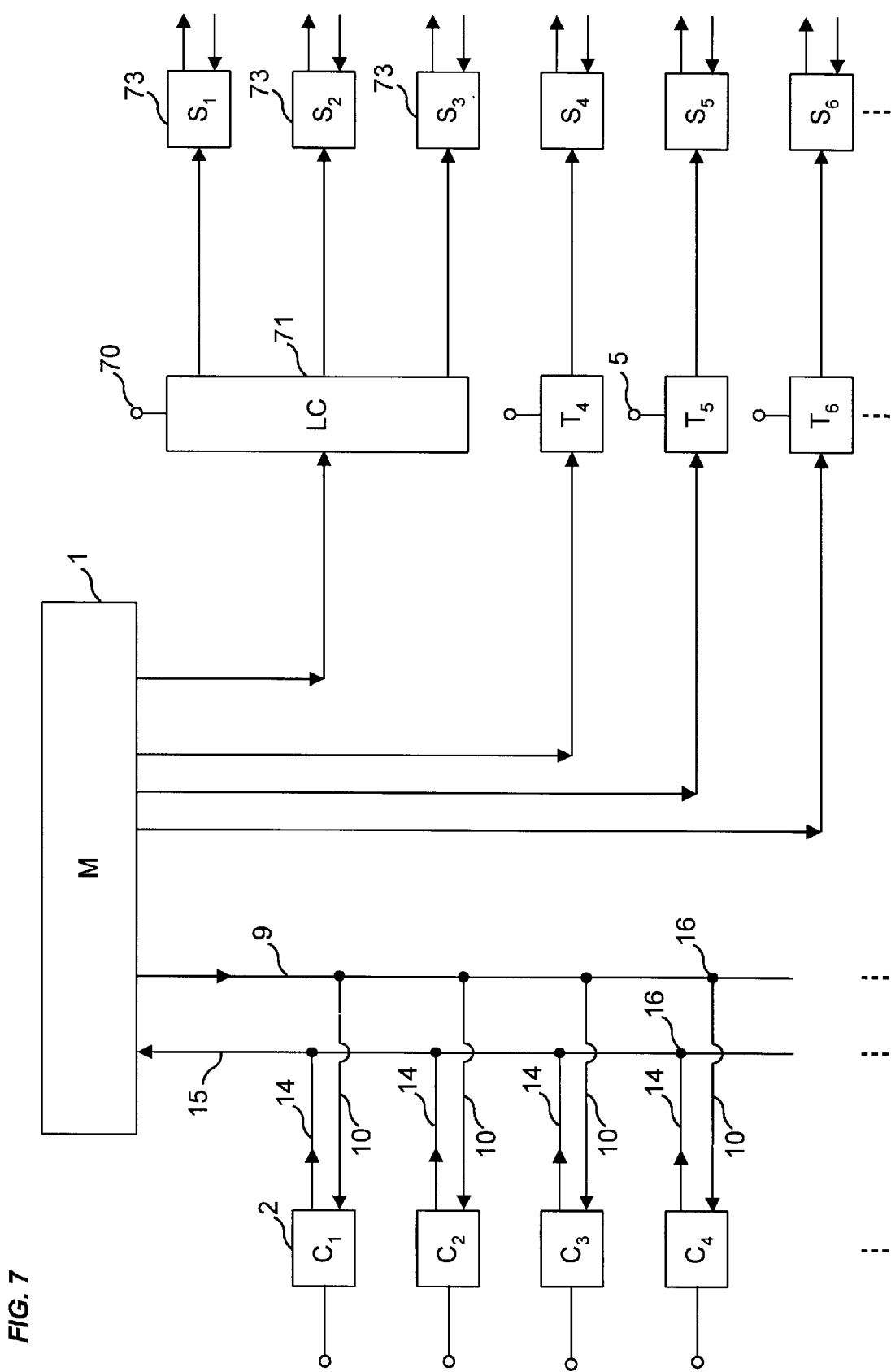
FIG. 7 is a schematic view of an exemplary system of the invention in which the Moderator transmits data to a computer associated with a plurality of switches.

In the implementation illustrated in FIG. 7, an adjunct computer 71, perhaps belonging to a local exchange carrier, receives the carrier selection data from the Moderator 1, further processes the data and controls Carrier selection in the switches 73 under its control. Routing tables in the switches 73 can be populated periodically by data from the adjunct computer 71 or the switch 73 can query the adjunct computer 71 as each call attempt is presented. The adjunct computer 71 can receive selection rules and other administrative directions from a local carrier administrator 70.

An alternative for end users to use of a PBX, a private switch, is subscription to Centrex service, in which the end users' originating switching point is a software-defined portion of the local central office switch of the local exchange telephone carrier. With data links between the adjunct computer 4 and the local central office switch, the end users' switch administrator can administer the end user portion of the processing capability of the bidding process in much the same way as if a PBX were being administered. In addition, instead of using a PBX or subscribing to a Centrex service, a residential or business customer could subscribe to a "least cost routing" feature offered by the local exchange telephone carrier as part of its enhanced calling services (currently including call waiting, call forwarding, 3-way calling, speed dialing, etc.). As with Centrex service the end users' switch enabling these enhanced calling features is a software-defined portion of the processing capability of the local central office switch.

The Moderator 1 also transmits received bids to the network management computers 2 of Carriers over the data link 9, 10. The exemplary architecture of FIG. 1 shows a combination of a single output data link 9 and individual Carrier input links 10 for this Moderator-to-Carriers bid data, indicating that the Moderator 1 may send the same data to all Carriers. There are many alternate transmission technologies available to transmit this bid data to all Carriers, including dedicated bidirectional links between the Moderator 1 and each Carrier, combining the function of links 7, 9, and 10.

Depending on the particular implementation, it may be appropriate to transmit all received bids to all Carriers. However, for example, each Carrier's bids need not be transmitted back to the bidding Carrier and there may be Carriers with limited service areas that are not interested in receiving bids from out-of-area Carriers. In any event, at least a portion of the bids are transmitted to a least a portion of the Carriers in order to implement an auction.

Figure 2:
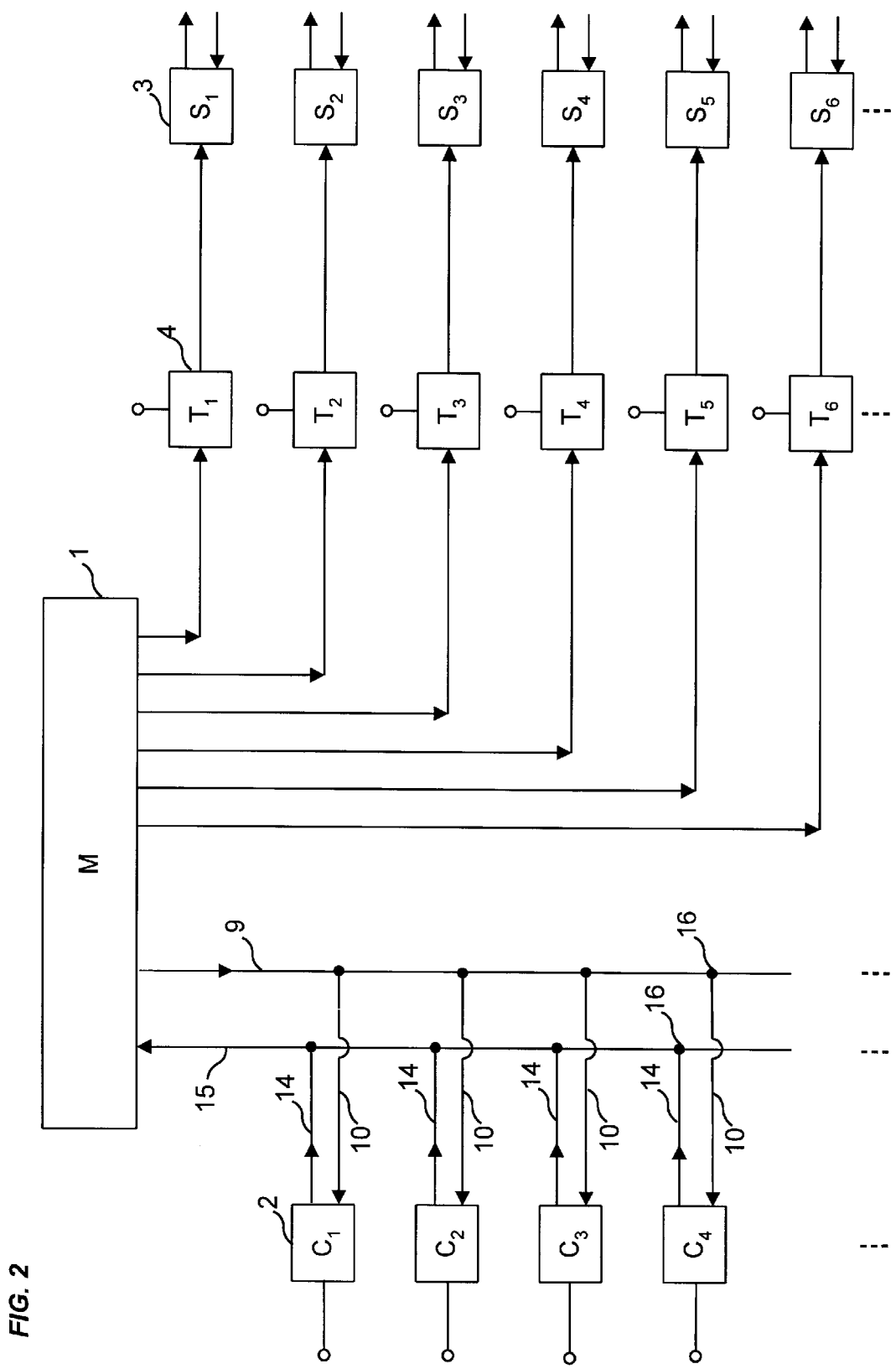
FIG. 2 is a schematic view of an exemplary system of the invention showing the Carriers using a shared data link to provide information to the Moderator.

FIG. 2 illustrates an alternative network architecture in which the individual Carrier-to-Moderator data links 14 share a common data input line 15 into the Moderator 1. This can be done, for example, by means of fiber optics using the SONET transmission protocol and ATM technology. This would require an ATM switching module at each junction 16 between the individual Carrier links 10, 14 and the common Moderator input-output links 9, 15. FIG. 2 illustrates bidirectional transmission using two transmission paths. However, such bidirectional transmission can be implemented over a single physical transmission line.

Figure 3:
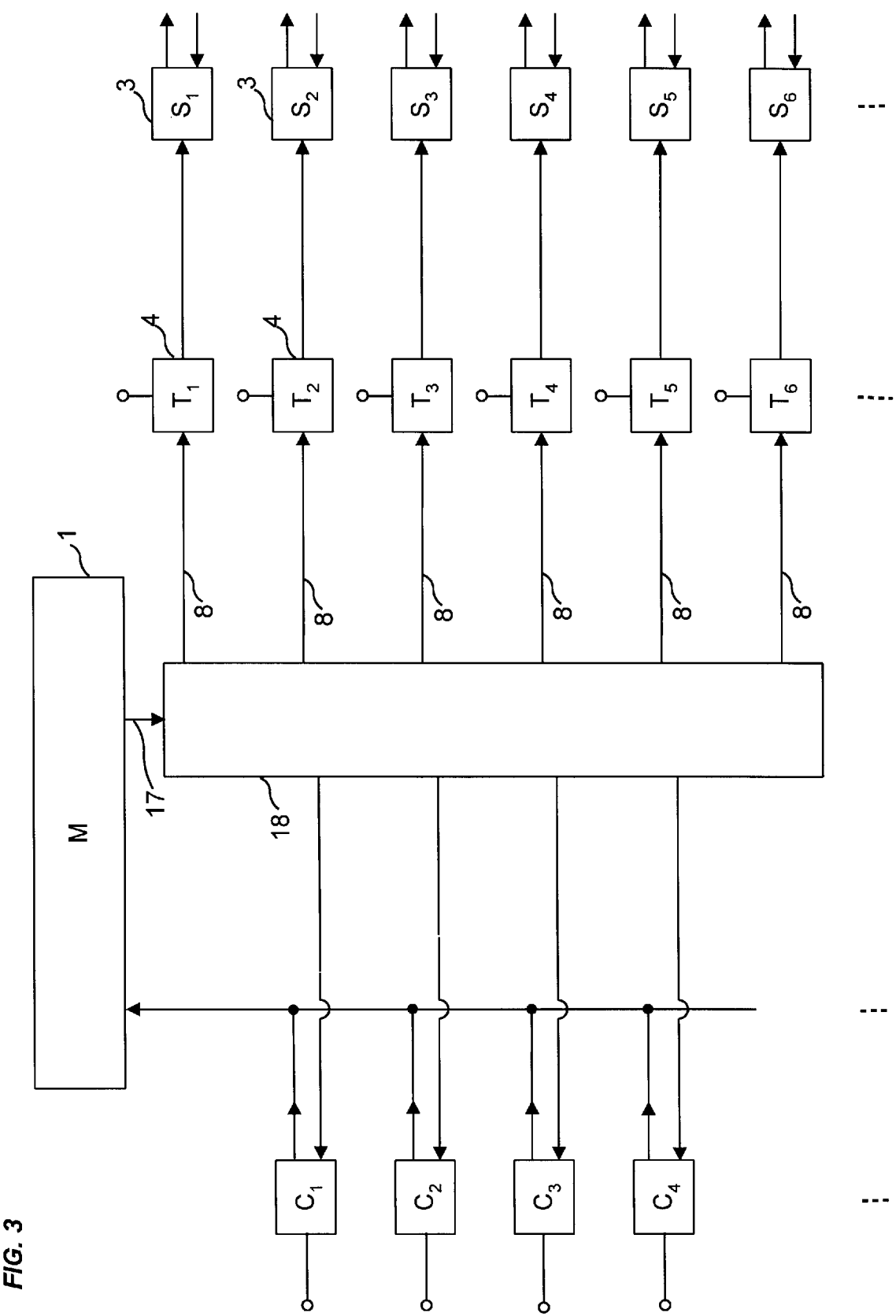
FIG. 3 is a schematic view of an exemplary system of the invention showing switched access from the Moderator to each of the subscribing switches and to each Carrier.

FIG. 3 illustrates an architecture incorporating switched access from the Moderator 1 to the switches 3. In this architecture a single Moderator output link 17 transmits each subscribing switch's bid data to a switch 18, which may be a dedicated switch or part of a public switched network. The bid information appropriate to each subscribing switch 3 is switched to each individual switch data link 8.

Figure 4:
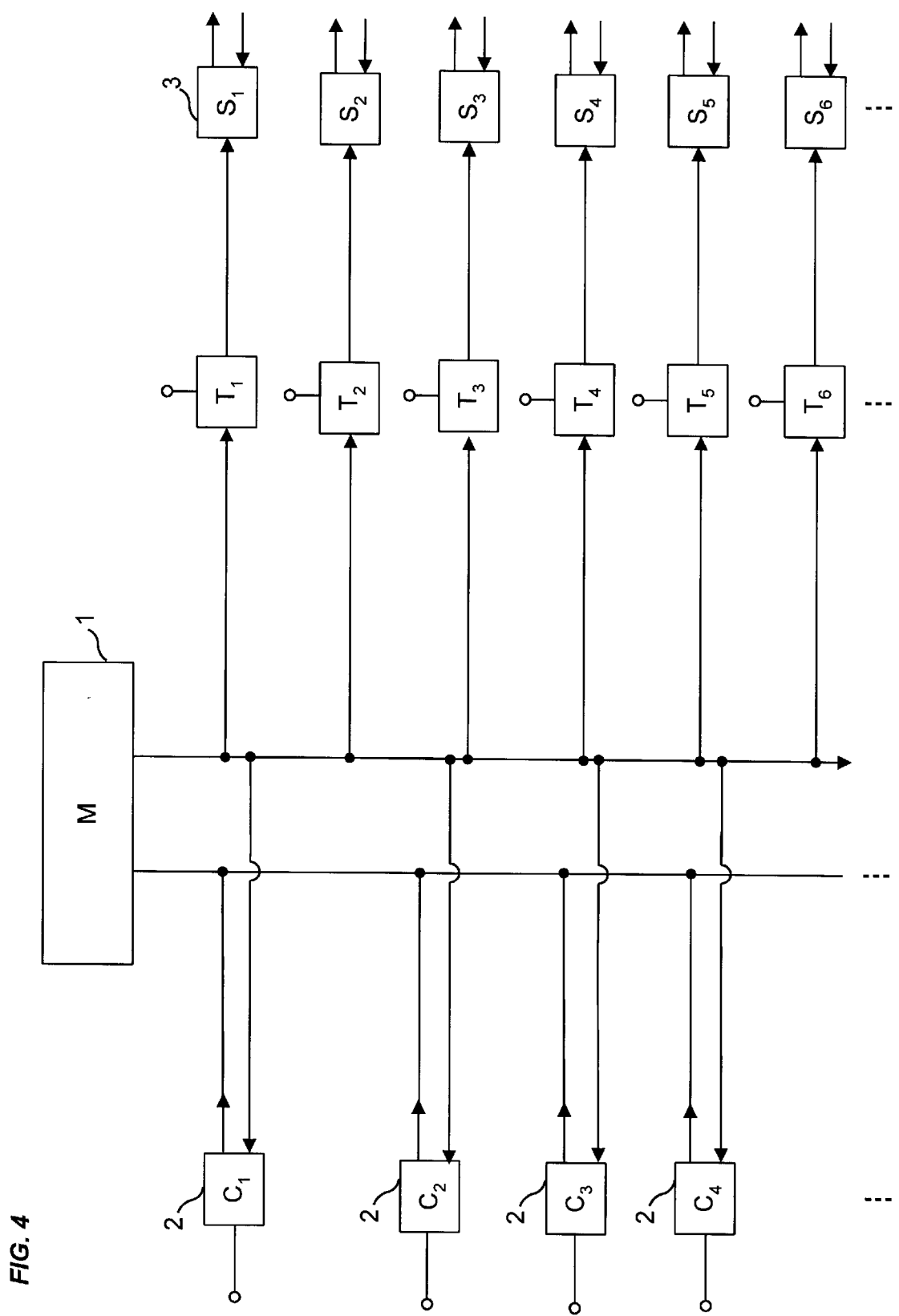
FIG. 4 is a schematic view of an exemplary system of the invention showing use of a shared data facility, such as a local area network, for communication from the Moderator to each of the subscribing switches and to each Carrier.

FIG. 4 illustrates use of shared facilities between the Moderator 1 and each of the switches 3 and the Carriers' network management computers 2. This could be accomplished, for example, by many known local area network (LAN), metropolitan area network (MAN), and wide area network (WAN) technologies.

The economic choices presented to telecommunication service users (and resellers) under this invention depend on bids submitted by Carriers for telecommunication traffic over the routes or route segments they serve as part of the various telecommunication-networks available to the users (and resellers). For purposes of differentiating in this document between a route and route segment, a "route" is service from the "originating switching point," i.e., the switching point on a telecommunications network that serves as the most immediate switching interface between the calling party and that telecommunications network (e.g., a local exchange switch or equivalent local switching node, whether hardware or software-defined, providing access to that network), to the "terminating switching point," i.e., the switching point on a telecommunications network (which may, but need not be, owned or operated by the same carrier who owns or operates the originating switching point) that serves as the most immediate switching interface between the called party and that telecommunications network (e.g., a local exchange switch or equivalent local switching node, whether hardware or software-defined, providing access to that network). A route may also have an originating point and a terminating point in the same local exchange area.

A local exchange switch (or equivalent local switching node) is generally considered to be (i) the switching point on a telecommunications network that serves as the most immediate switching interface between the calling party and that telecommunications network as well as (ii) the switching point on a telecommunications network (which may, but need not be, owned or operated by the same carrier who owns or operates the originating switching point) that serves as the most immediate switching interface between the called party and that telecommunications network, regardless of whether such telecommunications networks use circuit-switched, frame relay, asynchronous transfer mode, packet data, TCP/IP protocols or other current or evolving telecommunication technologies (e.g., optical or photonic switching). Local exchange switches (or equivalent local switching nodes), for example, may include telephone companies' local central office switches, private telecommunications networks' local access nodes, and Internet service providers' local access switches—whether represented by a server, router or other switching device (which may be hardware or software-defined), but in each case providing access to the respective telecommunications network.

To identify originating and terminating switching points for telephone calls within North America, for example, each local exchange switch on the public switched telephone network is designated in the North American Numbering Plan by a unique NPA-NXX code, where the NPA is a three digit numbering plan area identifier (e.g., area code 201 identifies a portion of Northern New Jersey) and NXX is a three digit code identifying a particular local exchange switch within the numbering plan area. It is common for a single local exchange switch to house more than one NXX Code. The interexchange Carriers that utilize this bidding process are usually identified by a Carrier identification code. This code may be, for example, a "1" signifying the end user's presubscribed or primary Carrier, a 7 digit code "101XXXX" for a Carrier other than the end user's primary Carrier, or some other code or data element designated for that purpose. Once a Carrier is selected for a call attempt, the appropriate Carrier identification code may be inserted in the call attempt's routing data (e.g., NPA-NXX-XXXX, the last four digits identifying the particular line served by the called party's NPA-NXX switch on the public switched telephone network).

The subscribing switch may also have dedicated direct links to one or more Carrier points of presence on any telecommunications network. If such a Carrier is selected, the subscribing switch would route the call attempt directly to that dedicated link (without, for example, being handled by the local exchange switch that may otherwise serve that subscribing switch).

While the currently predominant numbering scheme for originating and terminating switching points on the public switched telephone network is the North American Numbering Plan, other numbering schemes identifying originating switching points and terminating switching points are possible, particularly for other types of telecommunication networks, and may be used as telecommunication technology evolves. International telephone calling, for example, currently uses a country code and a city code before the code that identifies the local exchange switch on the public switched telephone network.

A "route segment" is any and all of the following: (i) service from an originating switching point on a telecommunications network to an "intermediate switching point" on the same or different telecommunications networks, such "intermediate switching points" being all switching points on one or more telecommunications networks that do not serve as the most immediate switching interface between the calling party and a telecommunications network or the most immediate switching interface between the called party and a telecommunications network, but do serve as switching points elsewhere in the telecommunications network or networks over which a call attempt may be routed (e.g., a tandem switch, a high-speed router or some other hardware or software-defined intermediate switching node on a telecommunications network); (ii) service from one intermediate switching point on a telecommunications network to another intermediate switching point on the same or different telecommunications networks; and (iii) service from an intermediate switching point on a telecommunications network to a terminating switching point on the same or different telecommunications networks. A route segment may also be entirely contained within one local exchange area. Each intermediate switching point in a telecommunications network has a unique identifier that is used in routing call attempts over route segments. Those identifiers can be used by the Moderator and the Carriers to manage the bidding process.

The competing Carriers bid for traffic by transmitting to the Moderator the economic incentive each Carrier will offer for traffic over each route or route segment it serves (or, at least, each route or route segment it wishes to compete for using the bidding process). The economic incentive presently contemplated as being most usual is the rate (amount of money charged per unit of time). However, many other kinds of economic incentive may be offered, such as a credit toward other services or a credit toward an additional rebate that may be offered if a user's traffic for a given month (or that of another telecommunication service provider reselling, for example, a Carrier's service between two switching points on that Carrier's telecommunications network facilities) rises above a threshold. The economic incentive could be a combination of rate and another incentive. But the economic incentive should be selected from a limited set authorized by the provider of the bidding mechanism, because the incentive must be capable of being evaluated by the software in the Moderator or in each subscribing switch's adjunct computer. A Carrier may wish to submit more than one bid for routes or route segments that start at switching points at which it offers more than one class or quality of service (e.g., switched service to some subscribers, dedicated access to others, high-speed service to still others, or combinations of different classes of service to some users). Each bid must be associated with a time period within which the bid will be effective.

The rules of the bidding process can be structured in many ways. The following are examples of possible bidding rules.

a) The day is divided into blocks of time by the bidding service provider and bids are submitted for each block of time. All bids for a given block of time must be submitted prior to a cut-off time that precedes that block of time by a protection interval. Any bid received after the cut-off time is considered to be effective for the next block of time, unless a new bid is subsequently received from the same Carrier for that route or route segment. The protection interval is needed to permit processing of the bid information by the Moderator and transmission of carrier selection data or bid information to the switch (or its associated adjunct computer) prior to the bid's start time. For example, if thirty minute blocks of time are auctioned, a five minute protection interval may be appropriate.

b) Carriers are permitted to submit bids for any time interval by specifying a start time and a termination time or a start time and a good-until-cancel instruction. However, no bid can be effective before a protection time interval specified by the bidding service provider. The bidding service provider can provide confirmation of received bids back to the Carrier if the data link from the Moderator to the Carriers is provided with a selective messaging capability.

c) Carriers may be permitted to enter default bids for any route or route segment and/or block of time for which they transmit no other bid.

d) As a fail-safe mechanism, to avoid use of old bids that have not been changed due to communication failure, the Moderator may impose a rule setting a time limit (a fail-safe protection time) to the applicability of any bid. At the expiration of the time limit, the expired bid could default to a preset default bid or to no bid. Such a rule could also be built into the switch software to protect against a failure in the Moderator-to-switch data link.

The principal data feedback from the Moderator to the Carriers is transmission of bidding data from the Moderator to each of the Carriers. This permits the Carriers to adjust their own bids for any particular route or route segment in view of other Carriers' bids for that route or route segment. In a block of time bidding scheme this transmission may take place, in different service offerings, either before or after the bid cutoff time for a given block of time. If transmitted before the cutoff time, the Carriers have an opportunity, up to the cutoff time, to adjust their bids for that block of time. If the service is arranged for transmission back to the Carriers after the cutoff time, the Carriers can adjust their bids for the next or subsequent blocks of time. If the bids are transmitted back to the Carriers after the cutoff time but before the bid's effective time, the Carriers would be able to manage their networks to take account of that time interval's bid structure. The bids can be adjusted to be higher or lower, dependent on whether the Carrier, in view of the state of its network traffic, wishes to further encourage or discourage additional traffic. The Carrier may wish to reduce its bid, for example, to encourage additional traffic on an underutilized telecommunication facility, or increase its bid to discourage traffic over a facility approaching a congested state. Depending on the transmission and computer technologies used, transmission by the Moderator (or an adjunct computer) back to the Carriers could also be accomplished by posting the bids on a bulletin board system or Internet website, making them available for retrieval by all Carriers.

An evolutionary development in local exchange switch architecture is the combination of a "dumb" switch and a "smart" peripheral computer. In this arrangement the switch accomplishes the actual connection between incoming and outgoing telecommunication facilities and the switch operating software performs the management functions specifically supporting the switching function. The peripheral computer contains the service-related software. This arrangement permits the telecommunication service provider to modify its service offerings without the need to ask the switch manufacturer to change the switch's operating software. Through use of an intelligent peripheral computer, one service, for example, that could be offered to all subscribers, including most businesses and individuals, is least cost routing. As in PBX least cost routing, the routing of a call attempt is dependent on population of a routing table. This least cost routing table is a memory file containing the cost (or other economic incentive) of call carriage over each route accessed by the switch or other carrier selection data. In accordance with the herein disclosed process, this routing table could be populated by the Moderator, based on carrier selection data it generates, or by a computer adjunct to the switch, based on decision rules entered by a switch administrator. Or, with appropriate software, the adjunct computer function could be incorporated in the switch's peripheral computer. With this combination of software implementations, a telecommunication service provider could offer a least cost routing service, at economically advantageous rates based on a bidding process, to all of its customers.

Figure 8:
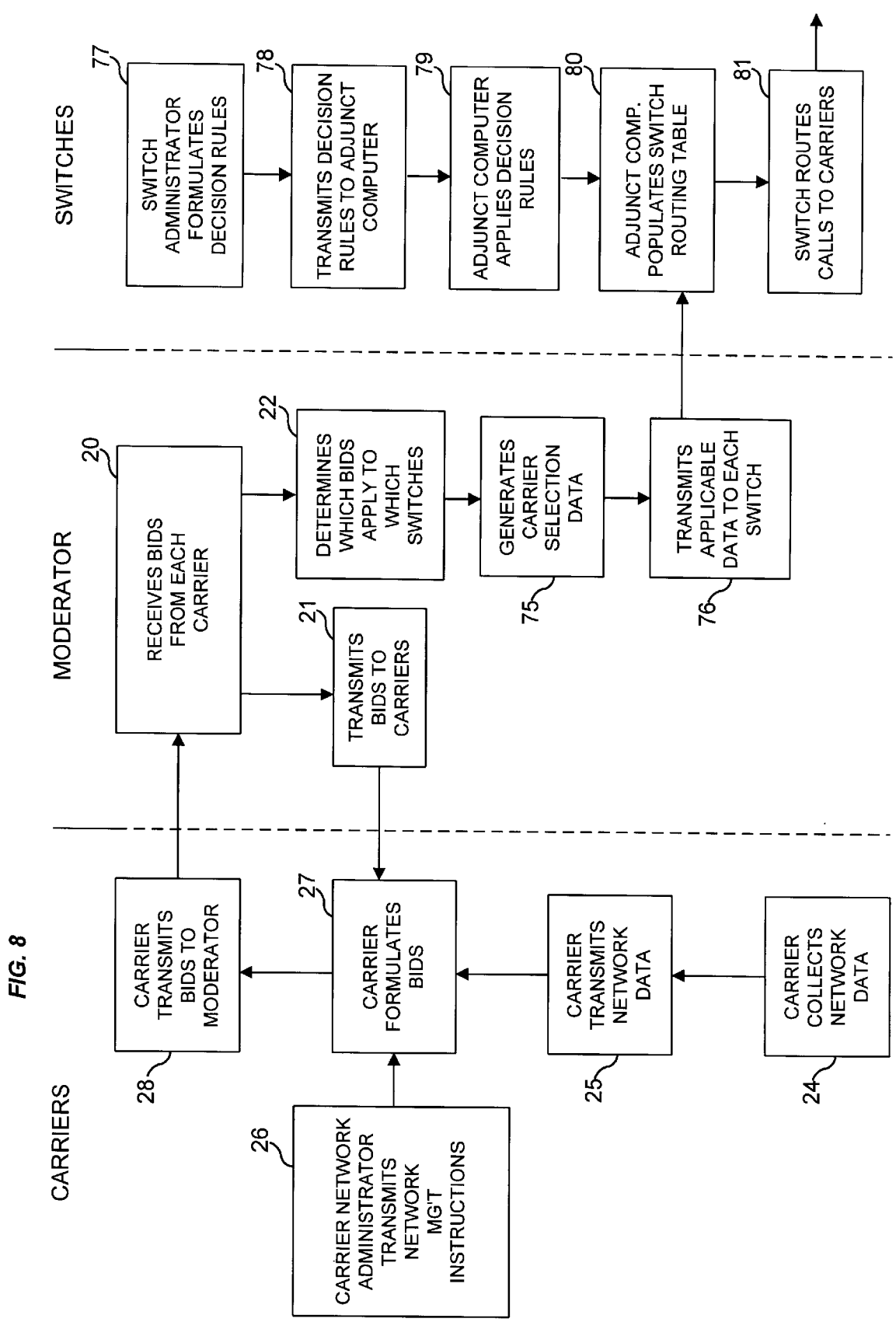
FIG. 8 is a schematic representation of an exemplary process of the invention in which the Moderator generates carrier selection data for the subscribing switches.

As illustrated in FIG. 8, the routing table can be populated with derivative data generated 75 in the Moderator by further processing of the economic incentive data. This could include carrier selection data, prioritizing the Carrier selection in accordance with Carriers' bids for each route or route segment starting at that switch. The applicable data can be transmitted 76 to each switch, including those in which the adjunct computer populates the switch's routing table 80. While some of the decision making process has been performed by the Moderator (i.e., sorting its bids and generating carrier selection data), the switch may make the ultimate Carrier selection 81 based on network conditions and decision rules from the administrator 77. The network architecture involved is as illustrated in FIG. 6, where the switch 3 represents the combination of the dumb switch and the intelligent peripheral computer and the input and output links 12, 13 represent all of the telecommunication facilities accessed by the switch 3. Another arrangement contemplated by the bidding process is for a local exchange carrier, controlling several switches, to receive the bidding or routing data for all its switches and further process that data for all of its switches.

The bid information being transmitted between the Moderator, the Carriers, and subscribing switches is sensitive business information and may need, under various circumstances, to be encrypted. Depending on how the service is arranged, there may be a need to protect the privacy of bids from interception by other participating Carriers or from interception by non-participating carriers. Some of the most sensitive information would be bid information sent from the Carriers to the Moderator, bid confirmation messages from the Moderator to the Carriers, and carrier selection data sent from the Moderator to the subscribing switching points. Some less sensitive information would be the bids broadcast back to all participating Carriers after the cutoff time for a given block of time. There are several encryption schemes known in the art for such use, including the RSA and PGP schemes.

Figure 5:
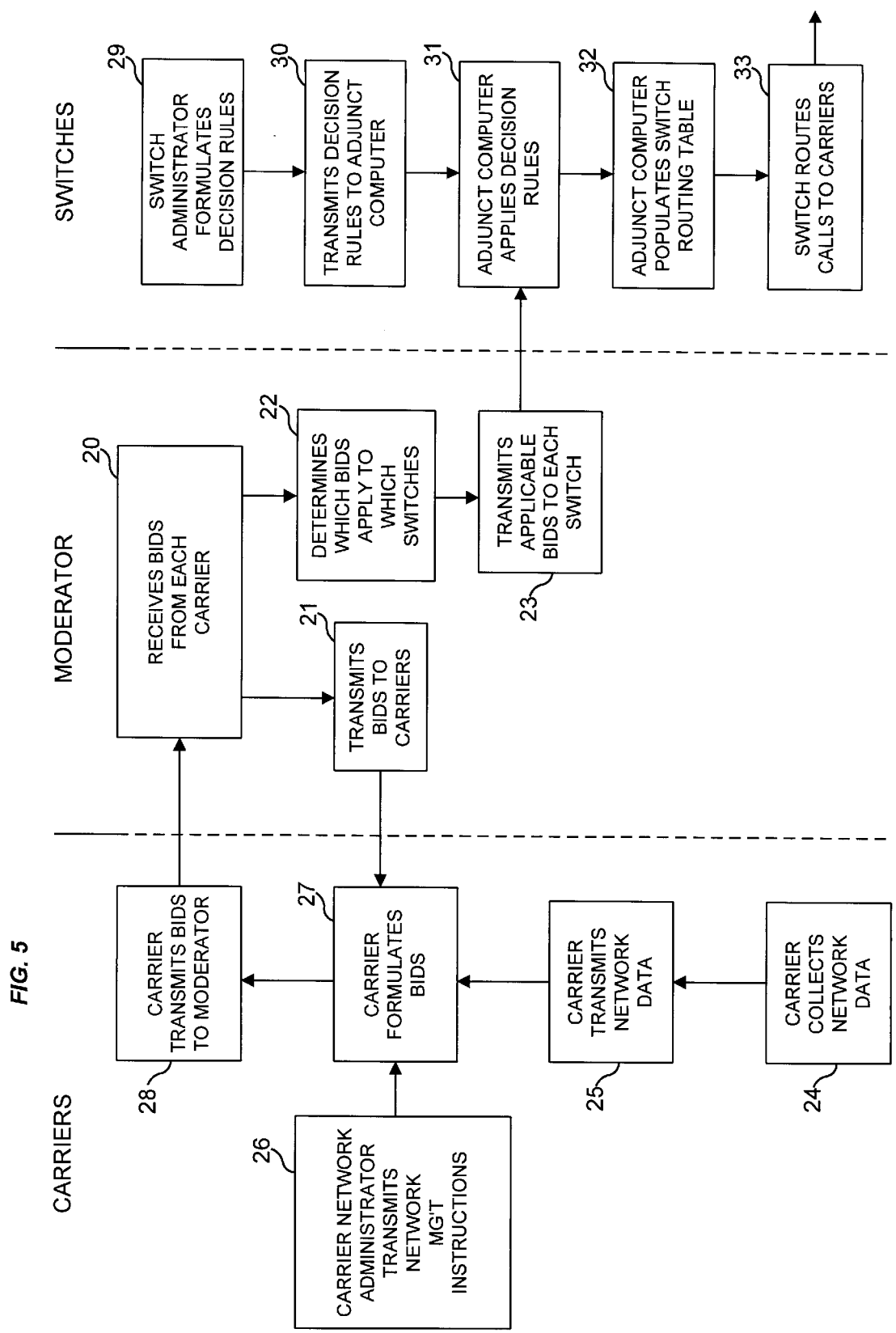
FIG. 5 is a schematic representation of an exemplary process of the invention showing transmission of bid information from the Moderator to the subscribing switches.

FIG. 5 illustrates an exemplary implementation of the bidding process of this invention. The process is carried out by participating Carriers, acting through their network management computers, the bidding service provider, acting through the Moderator computer, and the subscribing switches. The Carriers' primary purpose is to maximize revenue from the carriage of telecommunication traffic over their networks. The subscribing switches are usually managed to obtain telecommunication service most economically.

In operation of this exemplary bidding process, the Moderator receives bids 20 from each Carrier specifying the economic incentive the Carrier is willing to offer for carrying a call attempt over each route or route segment for which it wishes to place a bid. This information is stored in the computer's memory. At a time appropriate to the particular service arrangement in operation, the Moderator transmits 21 at least a portion of the bids received from the Carriers to at least a portion of the Carriers. The Moderator also processes the data in a sorting operation to determine which bids and/or carrier selection data derived from the bids are for routes or route segments that have a starting point associated with each subscribing switch and the Moderator transmits 23 the appropriate bids and/or carrier selection data to each such switch.

Each subscribing switch is operated by a switch administrator that formulates 29 the decision rules. A decision rule may be, for example, a simple instruction to switch a call attempt to the Carrier that has submitted the lowest cost bid. The rules may include, for example, an instruction to route all call attempts in a particular time period (e.g., from midnight to 6:00 A.M.) to a particular Carrier to satisfy the requirements of a contract between the switch's owner and that Carrier, or because this contract Carrier has contracted to carry all traffic during that time period for a flat monthly fee. At all other times, the decision rules might include an instruction to route call attempts to this contract Carrier only if its contract rate is lower than the lowest bid submitted to the Moderator by the other Carriers. The switch administrator may also instruct the switch or an associated adjunct computer to value a non-rate economic incentive in a particular way. If the Moderator transmits bid data without carrier selection data to the subscribing switch, the bids and decision rules are received by the switch or associated adjunct computer and stored in a data base in its memory. The switch or associated adjunct computer applies 31 the decision rules to the economic incentive data received as bids and generates the carrier selection data needed to populate the switch's routing table. The decision rules may be transmitted to the Moderator and the carrier selection data can be generated in the Moderator. The carrier selection data can be transmitted by the Moderator to the switch periodically, when generated, or in response to a query from the switch. The query can call for the carrier selection data in full or on a call-by-call basis. The routing table is the file that is accessed by the switch's routing software to decide which Carrier will receive a call attempt. The software may also provide for treatment of failed call attempts (e.g., retry, try the next lowest cost Carrier, or default to the contract Carrier). When a call attempt is presented to the switch, a routing decision is made and the call attempt routed 33 to a Carrier for transmission to the call's destination or to an intermediate switching point. In order to route a call attempt, the subscribing switch's operating software connects the input register carrying the call attempt to the output register connected to telecommunication facilities which connect to the selected Carrier for that route or route segment.

To reduce the exposure of end users (and resellers) to the potential volatility of prices offered via the bidding process, default Carriers may participate. If, for example, prices bid in the auction rise above a fixed upset price previously agreed to by the default Carrier, the Moderator could select the default Carrier as the winning bidder. The Moderator or owner of the subscribing switch may negotiate with one or more Carriers to serve as default Carriers. In the alternative, an end user or group of end users (or a reseller) may wish to specify to the Moderator or owner of the subscribing switch that a particular Carrier be designated as that end user's or reseller's default Carrier (e.g., a telecommunications service provider who has entered into a contract with the end user to carry a significant portion of that end user's telecommunications traffic outside of the bidding process).

The Moderator can also accommodate end users (and resellers) who wish to limit the group of Carriers from whom the Moderator will evaluate bids when a Carrier is to be selected for call attempts by such end users (or customers of such resellers). An end user (or reseller) may wish to request of the Moderator (or a subscribing switch's administrator) that each of its call attempts be routed only to one of a set of Carriers specified by that end user (or reseller). The Moderator, in compliance with this request, will include the bids of only this set of specified Carriers when generating carrier selection data for call attempts by such end users. The subscribing switch, when presented with a call attempt by such an end user, can include the calling party identifier as part of a query made by the switch to the Moderator for carrier selection data for this call. The Moderator can then associate this calling party identifier with data in its memory that reflects the limited set of Carriers specified by this end user, and provide carrier selection data to the querying switch based on the bids of this set of Carriers only.

The bidding process can also accommodate those end users (and resellers) who wish to employ a strategy of purchasing telecommunications service at the lower of the bid price in the auction or a negotiated price they agreed to pay a telecommunications service provider under a term contract. The Moderator or the subscribing switch can include this contract price received from such end user, along with the bids it evaluates each time telecommunications service is provided to this end user (or the customers of a reseller). If the contract price is lower than all of the other bids, the contract Carrier could be selected as the Carrier of choice for that end user (or reseller). If the contract price is higher than any of the other bids, the low bidder could be selected instead. The contract price could serve as a ceiling while the end user (or reseller) can still capture the benefit of low prices made available via the bidding process (e.g., at night when system wide excess capacity is greater than during peak daytime periods). To ensure that this end user (or reseller) can satisfy the volume commitments that would likely be part of any attractively-priced contract, the Moderator could enable this end user (or reseller) to designate from time to time (e.g., during certain peak demand daytime hours) that the contract price is to be treated as the low bid available to that end user (or reseller) at that time. At other times the Moderator will consider all bids submitted by other carriers as well as such contract price.

Routing decisions for each route or route segment of a call attempt may be made using the auction process at each switching point (i.e., at the originating switching point or any of the intermediate switching points on the same or different telecommunications networks) as a call attempt is presented to each respective switch. Routing decisions may also be made (e.g., by a central entity such as the Moderator) for all route segments comprising the entire route of a call attempt, from its originating switching point through any and all intermediate switching points to its terminating switching point, at each respective switching point before the call attempt is routed (e.g., in a manner conceptually similar to the call set-up process used today in SS7 signaling networks). Alternatively, routing decisions may be made using the auction process at any switching point for any group of route segments constituting less than all of the route segments comprising an entire route of a call attempt (e.g., for the remaining portion of a route from any intermediate switching point to its terminating switching point) before the call attempt is routed by that switching point.

Figure 9:
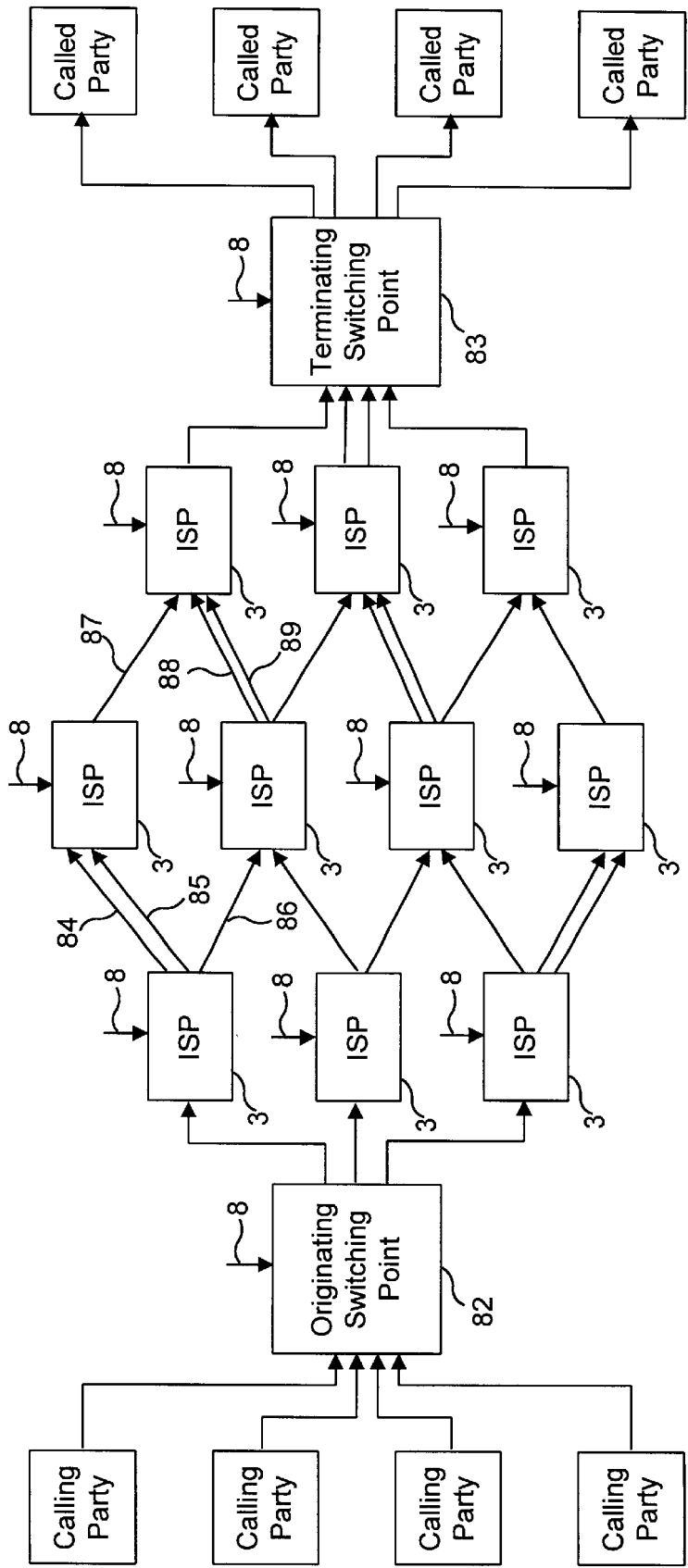
FIG. 9 is a schematic view of an exemplary network architecture in which routing decisions can be made at originating and intermediate switching points to select different route segments for call attempts presented to such switching points, based on data received from the Moderator.

As illustrated in FIG. 9, routing decisions for a call attempt can be made at an originating switching point 82 as well as at intermediate switching points 3 on one or more telecommunications networks, based on bid information and/or carrier selection data transmitted by the Moderator over a data link 8 to the respective switching point presented with the call attempt. ISP, as used in FIG. 9, stands for Intermediate Switching Point.

On certain types of telecommunication networks (e.g., packet data networks), a call attempt presented to a switch, for which a routing decision can be made, may consist of all or only part of the message or information (whether voice, data, video, etc.) being transmitted during the call by the calling party to the called party. For example, on packet data networks, when a calling party sends a data file to the called party, the network infrastructure would break up this file into a series of individual packets that are separately addressed and transmitted to the called party. Each of these packets may cross over different route segments in traveling from the originating switching point to the terminating switching point. Each packet can be treated as a call attempt by, for example, (i) the originating switching point for the entire route or (ii) by the originating switching point and each of the intermediate switching points to which the packet is presented for each of the route segments. And a routing decision can be made for each packet at each such switching point.

The transmission of bid information between the Carriers and the Moderator is a feed back process as illustrated, for example, in FIG. 5. Each Carrier transmits 28 its economic incentive bids to the Moderator and the Moderator transmits 21 received bids to each Carrier or at least the portion of the Carriers appropriate to each bid. The Carrier starts its bid formulation by collecting 24 network data, such as the capacity and traffic loading of each network facility, and transmitting 25 this network data to the Carrier's network management computer. The network data can be entered by keying it in or entered over a data link from the Carrier's network operations systems. The Carrier's network administrator enters (e.g., by keying them in or by data link) network management instructions, such as the fact that a particular facility is being taken out of service for maintenance or has a trouble that reduces its transmission capacity. The network management instructions could also be based on network performance characteristics, such as response time, or competitive business factors, such as the intent to compete more intensively for traffic to a specific region of the county or over routes or route segments that compete directly with another specified Carrier.

Software within each Carrier's network management computer then accesses its memory for the network data, the network management instructions, and the bid data received from the Moderator and determines 27 the economic incentive the Carrier will bid for traffic over each route or route segment. These data are accessed by means of the data buses and registers commonly internal to a computer. These bids are stored in the computer memory and transmitted 28 to Moderator. Since the network management computer has access to the bids of other Carriers, during each bidding cycle each Carrier has the opportunity to adjust its bids in view of the bids of the other Carriers for traffic over each route or route segment. This adjustment may be accomplished automatically by the software in response to the network management instructions, or may be accomplished by direct input from the network administrator viewing displayed bidding data. The result of such adjustment consideration may be a decision to leave the bid as originally calculated, as being appropriate to accomplish the network administrator's objective.

Figure 10:
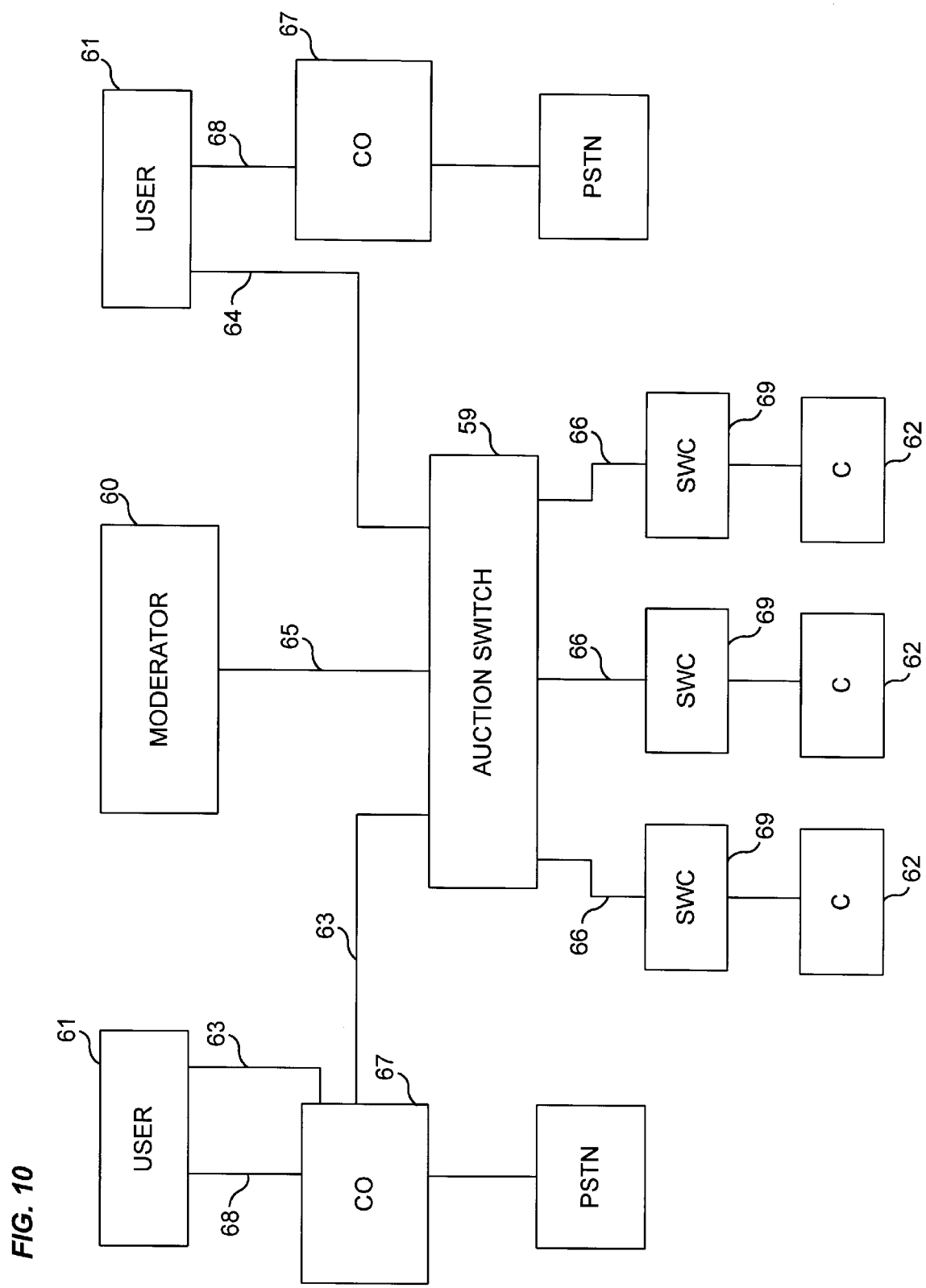
FIG. 10 is a schematic view of an exemplary network architecture in which a Moderator transmits data to a dedicated facility switch.

FIG. 10 illustrates a network architecture that enables large users 61 that route telecommunications traffic to Carriers 62 over dedicated access lines 63, 64 to take advantage of a bidding arrangement. This architecture can be employed by large users who wish to send their telecommunications traffic over different types of networks (e.g., circuit-switched, frame relay, asynchronous transfer mode, packet data, etc.) and use different classes of telecommunications service provided by such networks (e.g., transmission of voice, data, video, etc.). In this architecture a bidding Moderator 60 transmits the processed bidding data over a data link 65 independent of the dedicated access facilities 63, 64 carrying the call attempts from the users 61 to an auction switch 59 equipped with input and output ports adapted to receive dedicated facilities 63, 64, 66. The bidding data link 65 is also independent of any common channel signaling network associated with the dedicated facilities 63, 64, 66. The dedicated access facilities 63 may be connected, for example, through a local exchange telephone carrier's local central office 67 (or the equivalent local equipment of another provider of local access to a telecommunication network) or routed directly 64 from the user's PBX 61 (or other hardware or software-driven originating equipment) to the auction switch 59. The users 61 will, typically, also have switched access facilities 68 to a local exchange telephone carrier's local central office 67.

This dedicated facility auction switch 59 has a switching matrix for switching call attempts and a software directed switch controller for selecting a Carrier 62 for a call attempt, based on carrier selection data resulting from the bidding process, and routing the call attempt to the selected Carrier 62. The call attempt is switched to the dedicated Carrier facility 66 connected to the selected Carrier 62, perhaps by way of a serving wire center 69. Through this architecture large users 61 sending telecommunications traffic over dedicated facilities can benefit from the bidding process and, for traffic sent by users to the public telephone network, for example, such users can avoid the access charges imposed by local exchange telephone carriers on central office switched access traffic. Even though a dedicated facility 63 may connect through a local exchange telephone carrier's local central office 67, it is given a dedicated, unswitched connection, not triggering the imposition of a switched access rate element.

Some subscribing switches (referred to in this application as Auction Switches) may be provisioned to treat every call attempt presented to them as a call attempt which is to be routed to the low-bidding Carrier (e.g., a switching point dedicated for use only by calling parties or resellers who are customers of the Moderator's auction service). As illustrated in FIG. 10, a calling party may reach such an Auction Switch 59 using dedicated access facilities 64 from the calling party's premises equipment 61 (e.g., a PBX) to the Auction Switch 59. A reseller operating as a user of the Moderator's auction service (e.g., a local or long haul telecommunications carrier using the Moderator's auction service to lower its costs of obtaining telecommunications transport service from another carrier) may reach such an Auction Switch using dedicated facilities from the reseller's network equipment.

A calling party without such dedicated access facilities may reach an Auction Switch by means of a routing code stored at the originating switching point serving the calling party, with such routing code indicating to the originating switching point that call attempts from this calling party are to be routed first to the Auction Switch. In the existing public switched telephone network, for example, a calling party's local exchange switch (or an associated access tandem switch) recognizes the calling party's unique identifier (i.e., its own telephone number) and routes call attempts for destinations outside the local calling area to the local point-of-presence of the calling party's presubscribed or primary interexchange carrier, based on a unique carrier identification code stored at the switch identifying that carrier and associated with the calling party identifier by the calling party's local exchange carrier as part of its local switching infrastructure. Using a similar approach, a unique carrier identification code can also be designated for the Auction Switch. Calling parties who elect to become customers of the Moderator's auction service, but do not have dedicated access facilities to the Auction Switch, can be assigned the Auction Switch's carrier identification code. The calling party's local exchange carrier will then incorporate the Auction Switch's unique carrier identification code into its local switching infrastructure in lieu of the designation for that calling party of a presubscribed or primary interexchange carrier's unique carrier identification code. Thereafter, all call attempts by this calling party to non-local destinations will be routed by the local exchange switch to the Auction Switch, which can then route such call attempts to the low-bidding Carrier selected by the Moderator or the Auction Switch.

Figure 14:
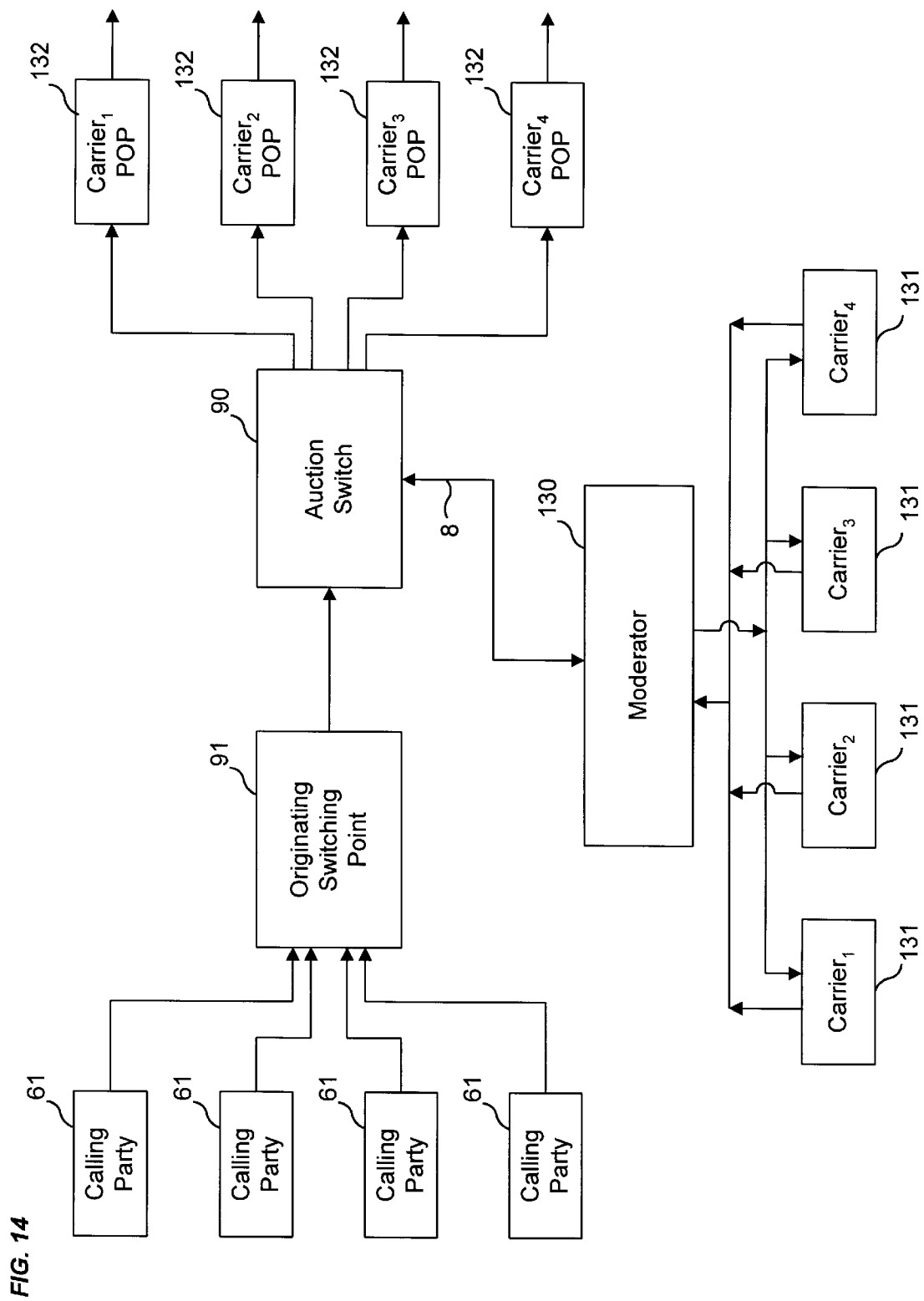
FIG. 14 is a schematic representation of an exemplary network architecture showing transmission of bid information from the Moderator to a subscribing switch receiving call attempts from a local exchange switch.
Figure 15:
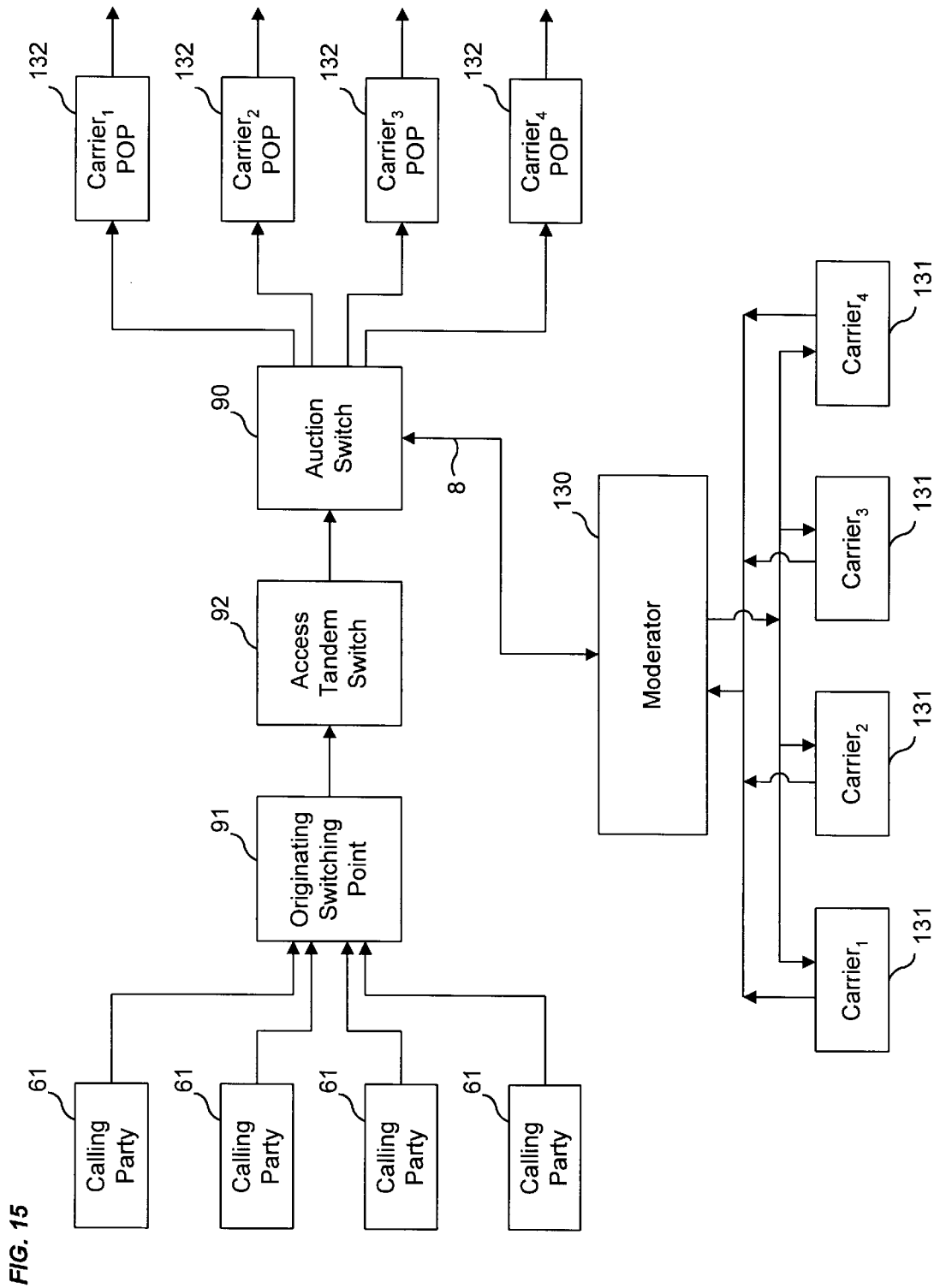
FIG. 15 is a schematic view of an exemplary network architecture showing transmission of bid information from the Moderator to a subscribing switch receiving call attempts from a local exchange telephone carrier's access tandem switch.

As illustrated in FIGS. 14 and 15, the routing decision for a call attempt can be made at an Auction Switch 90, based on bid information and/or carrier selection data transmitted by the Moderator 130 over a data link 8 to the Auction Switch 90 perhaps by an adjunct computer with a data link to the Auction Switch. When the local telecommunication carrier's local exchange switch (or equivalent local switching node) 91 receives a call attempt from the calling party, this local switch associates the calling party's unique identifier (e.g., its telephone number or packet origination address) with the unique carrier identification code for the Auction Switch and routes the call attempt to the Auction Switch 90, as illustrated in FIG. 14. If non-local call attempts are sent by that local carrier's local exchange switch (or equivalent local switching node) 91 to the carrier's access tandem switch 92 before the local carrier associates the calling party identifier (i.e., its telephone number or packet origination address) with the carrier identification code for the calling party's presubscribed or primary interexchange carrier (or equivalent long-haul carrier, if using a network other than the existing public switched telephone network), the access tandem switch can associate the calling party identifier with the carrier identification code for the Auction Switch and then route the call to the Auction Switch 90.

In the existing public switched telephone network, a calling party can override its presubscribed or primary interexchange carrier designation by inputting a different carrier identification code before the call attempt's routing data when attempting to make a call (e.g., inserting a 7-digit code "101XXXX" identifying the alternative carrier before the particular NPA-NXX-XXXX being dialed). In the same fashion, a calling party using the existing public switched telephone network, who wishes to make use of the Moderator's auction service only as an alternative to the calling party's presubscribed or primary interexchange carrier, may do so by inputting the Auction Switch's unique carrier identification code before the call attempt's routing data (e.g., the particular NPA-NXX-XXXX being dialed). This call attempt will then be routed to the Auction Switch 90, which can then route such call attempt to the selected low-bidding Carrier's point of presence 132.

In many public switched telephone network architectures a local exchange carrier will use an access tandem switch serving several local exchange switches to supplement the computing capabilities of the local switches it serves. In such cases all calls requiring routing outside of each local exchange switch's local serving area are sent to the access tandem switch. The access tandem switch contains the network intelligence and information needed to route such calls to other switches, including Carriers' points of presence.

The public switched telephone network architecture is an example of a more general telecommunications architecture placing different levels of intelligence and functionality at different positions in the architecture. For the purposes of this application, the term "access tandem" should be read to mean the first switching point in any telecommunications network architecture at which a decision is made to route a call attempt to one of several possible Carriers or to an Auction Switch, other than the originating switching point (e.g., the local exchange switch or equivalent local switching node) for such call attempt.

In some cases, the Subscriber function can be incorporated in a more capable switching point (e.g., a local exchange switch or equivalent local switching node) handling call attempts from calling parties or resellers who are customers of the Moderator's auction service and from other calling parties who are not. In that case, when a call attempt is presented to such a Subscriber capable switching point, the Subscriber can use the calling party's unique identifier (e.g., the calling party's telephone number or packet origination address) to determine whether this calling party is or is not a customer of the Moderator's auction service.

Many local telecommunications service providers (e.g., local exchange telephone carriers), use intelligent network architectures well known in the art to offer multiple features or classes of service to their customers based on the capability of the service provider's local switching infrastructure to recognize the calling party's unique identifier (e.g., its telephone number or packet origination address). Each calling party can elect to subscribe for one or more of the available classes of service. The local service provider's switch (with its intelligent network capabilities) can associate the calling party's unique identifier with the specific classes of service to which that calling party has subscribed. One such class of service which local telecommunications service providers, such as local exchange telephone carriers, could offer to calling parties is the Moderator's auction service.

Figure 16:
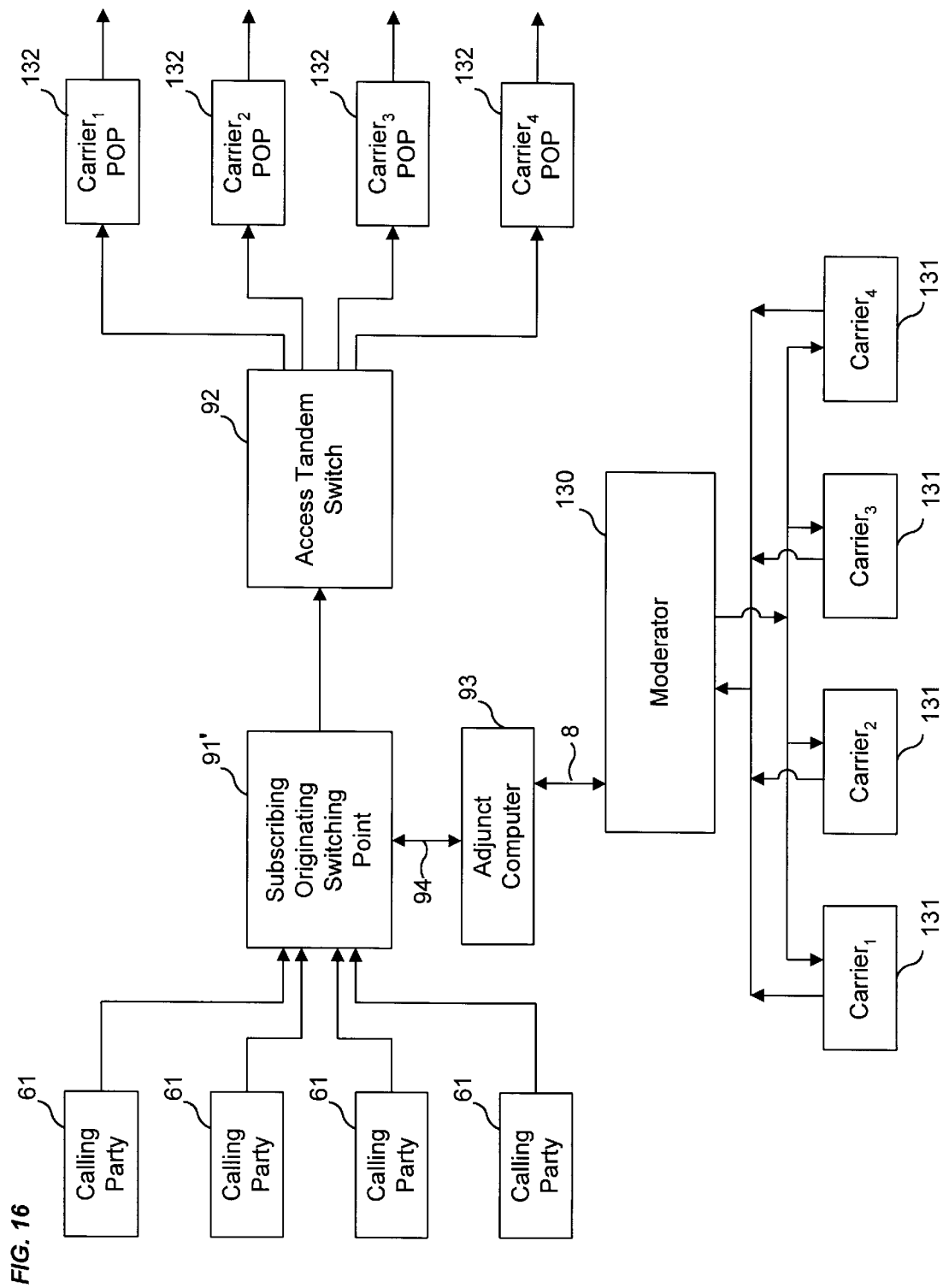
FIG. 16 is a schematic representation of an exemplary network architecture in which the Moderator transmits data to a local exchange switch of a local exchange telephone carrier.
Figure 17:
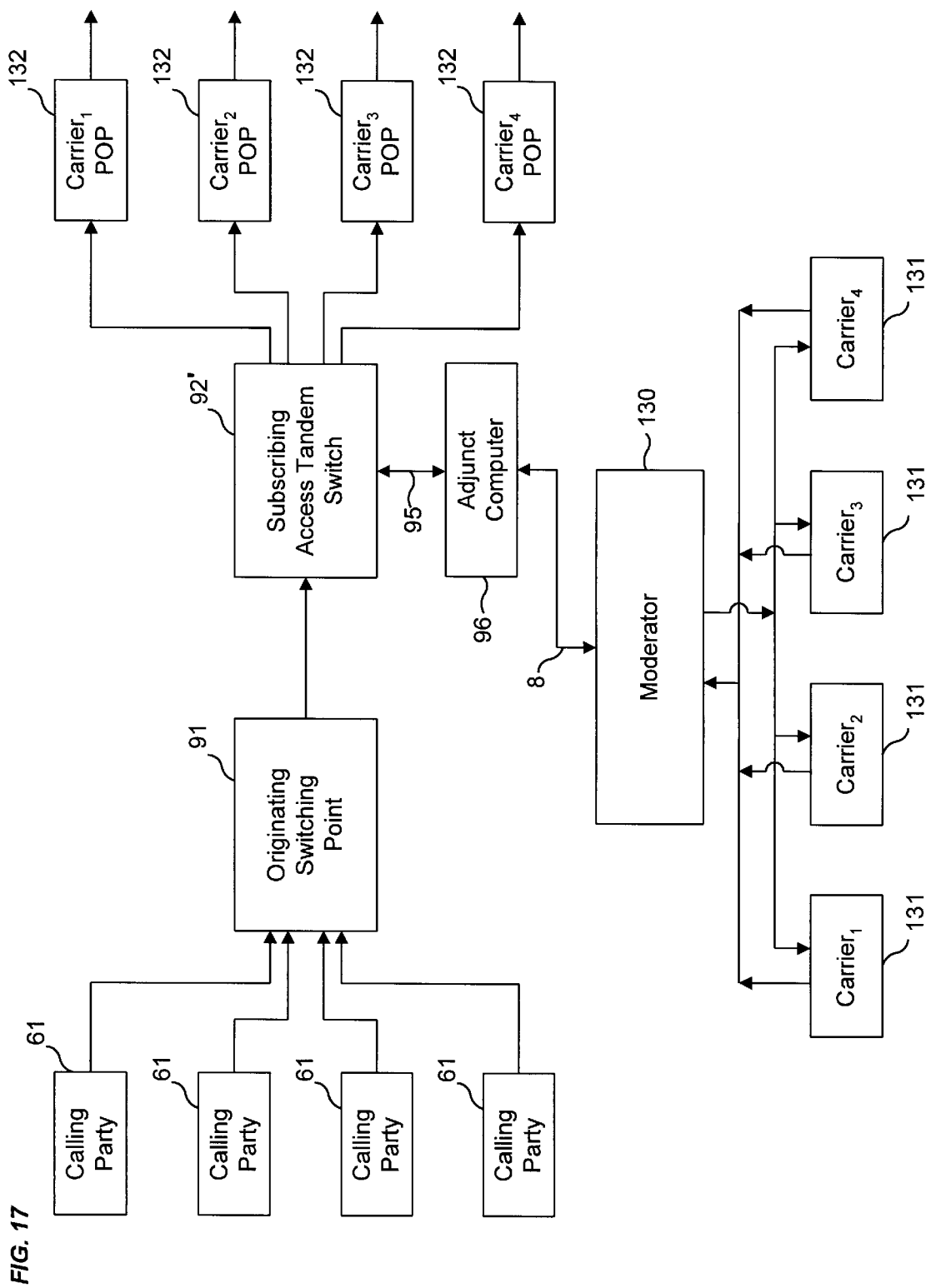
FIG. 17 is a schematic view of an exemplary network architecture in which the Moderator transmits data to an access tandem switch of a local exchange telephone carrier.

As illustrated in FIG. 16, the routing decision for a call attempt using the Moderator's auction service can be made at the local telecommunication carrier's local exchange switch (or equivalent local switching mode, if using a telecommunications network other than the existing public switched telephone network) 91' which, through a software defined portion of its software control, can serve as a subscribing switching point for a calling party who subscribes for a class of service utilizing the Moderator's auction service. Such routing decision can be based on the bid information and/or carrier selection data transmitted by the Moderator 130 over a data link 8 to the suitably enhanced local switch (a Subscriber-capable switch) 91', perhaps by way of an adjunct computer 93 with a data link 94 to the local switch 91'. As illustrated in FIG. 17, if a local telecommunications carrier implements this class of service at its access tandem switch 92', which has been suitably enhanced to incorporate the Subscriber function, the routing decision for a call attempt can be made in a software defined portion of the access tandem switch 92', based on bid information and/or carrier selection data transmitted by the Moderator 130 over a data link 8 to the suitably enhanced tandem switch 92' (the subscribing tandem switch), perhaps by way of an adjunct computer 96 with a data link 95 to the tandem switch 92'.

The routing decision for a call attempt can also be made at an Auction Switch, as illustrated in FIGS. 14 and 15, based on bid information and/or carrier selection data transmitted by the Moderator 130 over a data link 8 to the Auction Switch 90, perhaps by way of an adjunct computer with a data link to the Auction Switch. When the local telecommunication carrier's local exchange switch (or equivalent local switching node, if using a telecommunications network other than the existing public switched telephone network) 91 receives a call attempt from the calling party, this local switch can associate the calling party's unique identifier (e.g., its telephone number or packet origination address) with the class of service utilizing the Moderator's auction service, and then route the call attempt to the Auction Switch 90. If non-local call attempts are sent by that local carrier's local exchange switch (or equivalent local switching node) 91 to the carrier's access tandem switch 92 before the local carrier associates the calling party's identifier with such a class of service, the tandem switch will associate the calling party identifier with the class of service utilizing the Moderator's auction service, and route the call to the Auction Switch 90. In either case, the Auction Switch 90 can then route such call attempt to the low-bidding Carrier 132 selected by the Moderator or by the Auction Switch.

In some telecommunications networks, such as packet data networks (e.g., networks used to carry IP packets, ATM cells, frame relay frames, etc.), each call attempt can include data fields in addition to an unique calling party identifier (e.g., a packet origination address) and a called party (or destination) address. One or more of the switches through which a call attempt passes can process some or all of the information in these additional data fields and route the call attempt in accordance with such information. For example, call attempts requiring a higher quality of service than others (e.g., IP packets that are part of a video transmission) may include in each packet such an additional data field with a high-priority service type indicator or code. One or more of the switches through which these packets pass will process that data field indicator and then route such packets to less congested transmission paths (with fewer delays and/or packet loss) than those paths over which lower priority traffic might travel. Some or all of the information in these additional data fields processed by the switch can indicate to the switch that the call attempt is to be routed in accordance with the Moderator's auction service. For purposes of this application, the term "data field indicator" is not intended to include the calling party's identifier (e.g., its telephone number or packet origination address), the called party (or destination) address, or the carrier identification codes used in the existing public switched telephone network to identify a calling party's presubscribed or primary interexchange carrier.

As illustrated in FIG. 16, the routing decision for a call attempt using the Moderator's auction service can be made at the local telecommunication carrier's local exchange switch (or equivalent local switching node, if using a telecommunications network other than the existing public switched telephone network) 91' which, through a software defined portion of its software control, can serve as a subscribing switching point for a calling party who transmits a call attempt containing a data field indicator indicating that this call attempt is to be routed in accordance with the Moderator's auction service. When such a call attempt is received at the suitably enhanced local switch (a Subscriber-capable switch) 91', that switch can process this data field indicator (without associating the data field indicator with a calling party indicator) and route the call attempt accordingly. Such routing decision can be based on the bid information and/or carrier selection data transmitted by the Moderator 130 over a data link 8 to the local Subscriber-capable switch 91', perhaps by way of an adjunct computer 93 with a data link 94 to the local switch 91'. As illustrated in FIG. 17, if a local telecommunications carrier implements the processing of this data field indicator at its access tandem switch 92', which has been suitably enhanced to incorporate the Subscriber function, the routing decision for a call attempt can be made in a software defined portion of the access tandem switch 92', based on bid information and/or carrier selection data transmitted by the Moderator 130 over a data link 8 to the enhanced tandem switch 92' (the subscribing tandem switch), perhaps by way of an adjunct computer 96 with a data link 95 to the tandem switch 92'. In the alternative, the local Subscriber-capable switch 91' or the access tandem Subscriber-capable switch 92' in FIGS. 16 and 17, respectively, can process the data field indicator and route the call attempt as described above in this paragraph, based on bid information and/or carrier selection data supplied by the Moderator (or adjunct computer), but after first associating the unique calling party identifier (e.g., its packet origination address) with the data field indicator to confirm that the calling party identifier is associated with a calling party that is an authorized auction service user.

The routing decision for such a call attempt (i.e., containing a data field, in addition to a calling party identifier or a destination address, indicating that this call attempt is to be routed in accordance with the Moderator's auction service) can also be made at an Auction Switch, as illustrated in FIGS. 14 and 15, based on bid information and/or carrier selection data transmitted by the Moderator 130 over a data link 8 to the Auction Switch 90, perhaps by way of an adjunct computer with a data link to the Auction Switch. When the local telecommunication carrier's local exchange switch (or equivalent local switching node, if using a telecommunications network other than the existing public switched telephone network) 91 receives a call attempt from the calling party, this local switch can process the data field indicator indicating that this call attempt is to be routed in accordance with the Moderator's auction service (without associating the data field indicator with the calling party's unique identifier, such as its packet origination address), and then route the call attempt to the Auction Switch 90. If non-local call attempts are sent by that local carrier's local exchange switch (or equivalent local switching node) 91 to the carrier's access tandem switch 92 before the local carrier associates the calling party's identifier with such data field indicator, the tandem switch will associate the calling party identifier with the data field indicating that this call attempt is to be routed in accordance with the Moderator's auction service, and route the call to the Auction Switch 90. In the alternative, the local exchange switch (or equivalent local switching node) or the access tandem switch, as the case may be, can process the data field indicator and route the call attempt to the Auction Switch, but after first associating the calling party's unique identifier with the data field indicator. In each case, the Auction Switch 90 can then route such call attempt to the low-bidding Carrier 132 selected by the Moderator 130 or by the Auction Switch.

In selected cases, a Subscriber-capable switch may be instructed to treat call attempts received from callers identified as customers of one or more telecommunication service providers (e.g., customers of a switchless reseller) as calls for which routing decisions are to be based on the Moderator's auction service. These call attempts might reach the Subscriber-capable switch via public switched access facilities or dedicated facilities from the telecommunications service provider originating the call attempt, or from the service provider carrying the call attempt over the route segment ending at the Subscriber-capable switch. The switch may distinguish between those call attempts that are to be routed based on the auction process, and those that are not, by any of several means (e.g., calling party identifier or the carrier-specific facilities, if any, over which the call attempt is received).

In certain other cases, a Subscriber-capable switch may be instructed to treat call attempts that have one of a set of destinations specified by the Moderator or the switch administrator, as subject to the auction process. This may be done, perhaps, at the request of the end user or the telecommunications service provider originating the call or carrying the call to the Subscriber-capable switch (e.g., the Subscriber, situated in New York City, will select the low-bidding Carrier for all call attempts it receives that have destinations in downtown Chicago). Such a call attempt can reach the Subscriber-capable switch using any of the methods described in the preceding paragraphs.

Figure 12:
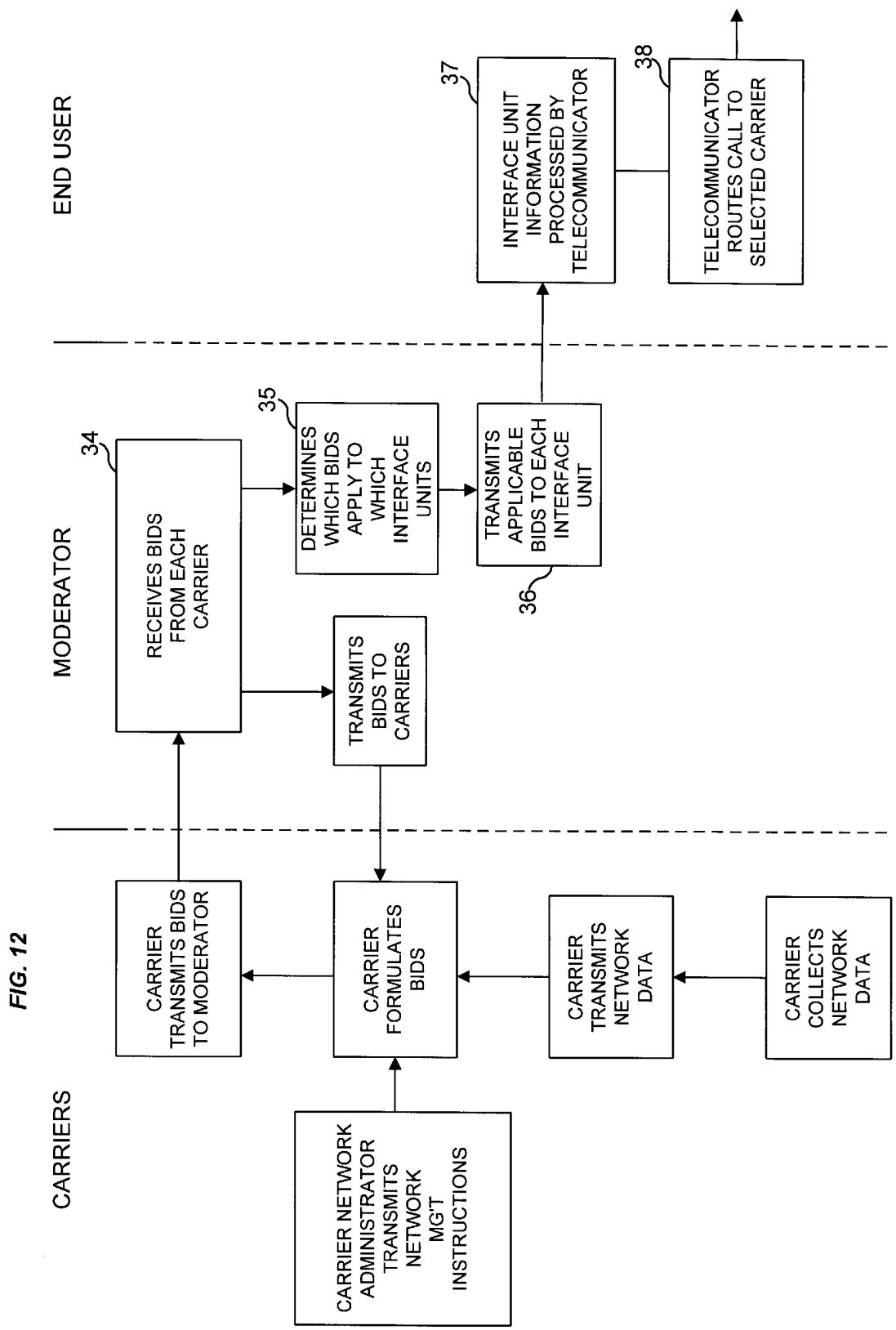
FIG. 12 is a schematic representation of an exemplary process of the invention showing transmission of information from the Moderator directly to end users.

FIG. 12 illustrates a process by which the Moderator transmits bids directly to end users for traffic originating in a specified local exchange area (e.g., an NPA-NXX or group of NPA-NXXs on the public switched telephone network, including a group comprising all NPA-NXXs in the North American Numbering Plan) and terminating anywhere. Here the Moderator receives bids 34 as before. However, the bids are independent of terminating point. The Moderator processes the data to sort it by originating point to determine 35 which bids apply to which end users, each end user having an interface unit to receive and store the data. The Moderator then transmits 36 the bid data and/or carrier selection data for a particular local exchange area to the interface units of all subscribing end users in such local exchange area (e.g., all subscribing end users served by the local exchange switch for a specific NPA-NXX), as interface unit information. The information may be displayed for evaluation by the end user or processed, within the interface unit, with direction from the end user, and all outgoing calls routed to the selected Carrier. If the Carrier information is displayed for the end user, the end user can choose a Carrier for a call attempt and key in the selected Carrier's carrier identification code before the desired destination address (e.g., telephone number). If the information is processed automatically within an interface unit, in the line or wireless connection between the end user's terminal equipment and the local exchange switch (or equivalent local switching node) or a Carrier's point of presence, the interface unit can, for example, automatically insert the appropriate carrier identifier in the outgoing telephone numbers. The interface unit could be a stand-alone piece of equipment, an attachment incorporated into the end user's terminal equipment or a software-defined portion of the end user's terminal equipment.

At the end user, the degree of automation of the process depends on the particular telecommunication terminal equipment being used. If the terminal equipment is a simple telephone, the telecommunicator function 37 specified in FIG. 12 may consist of the end user reading the bids from a display screen in the interface unit, making the routing decision, and routing 38 the call attempt by keying in the selected Carrier access code. If the terminal equipment is more complex, such as a personal computer or other microprocessor-containing equipment, the decision can be software implemented. The Carrier access code could be inserted by the terminal equipment or by the interface unit, if the interface unit is in the end user's telecommunication access line or wireless connection to the telecommunication network.

Figure 13:
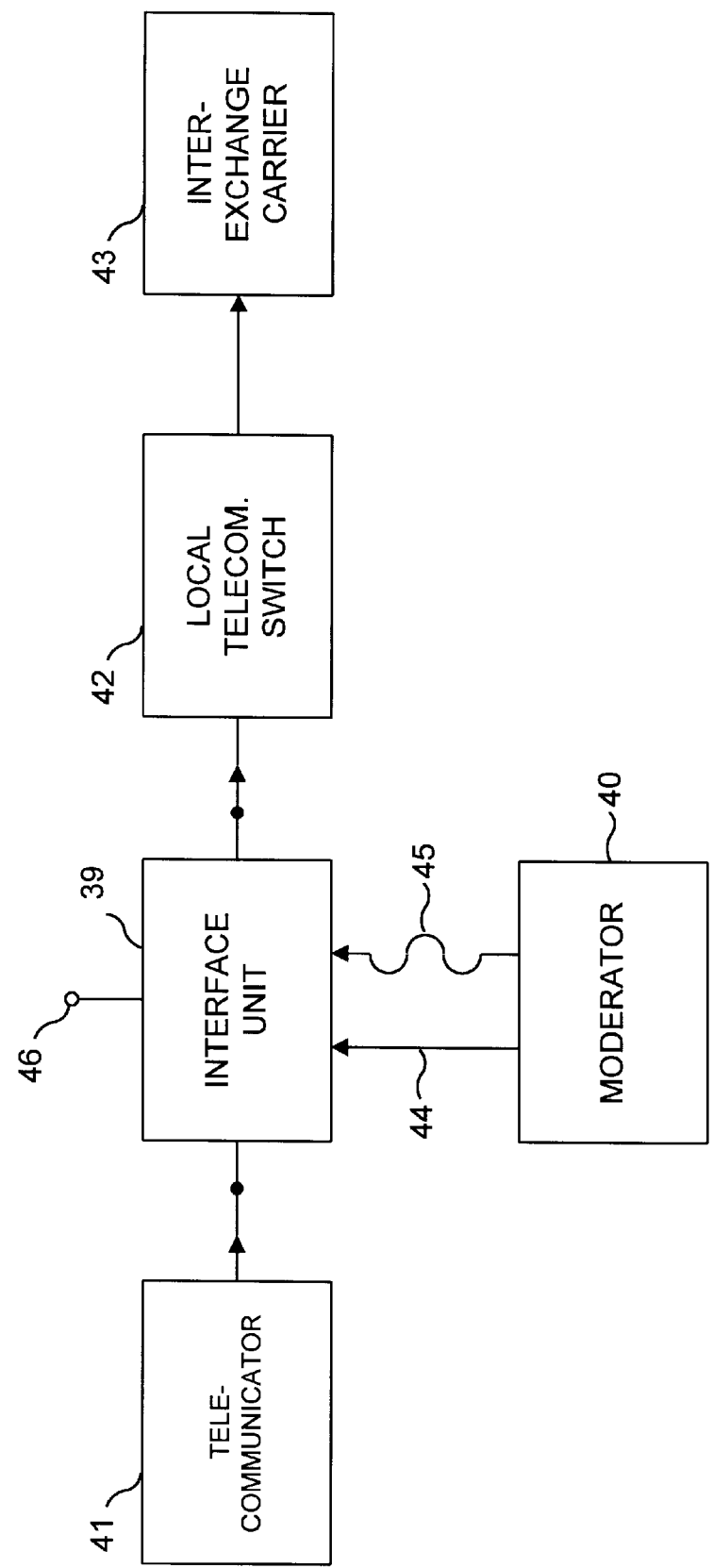
FIG. 13 is a schematic view of an exemplary end user portion of a system of the invention.

FIG. 13 illustrates the interface unit's position within the bidding architecture of FIG. 12. The interface unit 39 receives bid data or carrier selection data from the Moderator 40 over a telecommunication facility that may be a wire link 44 or a wireless link 45. The interface unit has either a wired input port or contains a wireless receiver (e.g., radio or optical). The interface unit 39 is in the telecommunication path between the telecommunicator and the external telecommunication network, such as the local exchange switch 42 that routes the call to the selected Carrier 43 in response to the Carrier access code. The interface unit may have a separate end user input port 46 for use by the end user to key in the selected Carrier access code each time a call is placed. The end user may also be able to key in a Carrier selection and the interface unit may contain a tone generator or digital signal generator necessary to automatically insert the Carrier access identification code for each call attempt. The interface unit 39 may also have a screen to display the bid information to the end user.

In order not to require each end user or reseller subscribing to the bidding process to establish a billing arrangement with each Carrier taking part in the bidding process, a central billing arrangement is advantageous. Such billing arrangements can be implemented with bill preparation performed by the Moderator, by an independent billing service provider, by the end user or reseller (e.g., a local exchange carrier owning or operating a subscribing switch) or by the selected Carrier. In each billing arrangement described herein, implementation may be facilitated by employing computers associated with the Moderator or with the switches, billing or operations support systems of the Carriers, the end users or resellers, or of any independent billing service entities. Such associated computers may be separate items of hardware or may be software-defined portions of the Moderator or of the switches, billing or operations support systems of the Carriers, the end users or resellers, or of any independent billing service entities. In each billing arrangement described herein, the call source may be the telecommunications equipment or facilities being used by (i) an end user calling party, (ii) a local exchange switch (or equivalent local switching node), or (iii) any intermediate switching point between a calling party and a called party.

Bills may be rendered (a) on a retail basis to the end user or (b) on a wholesale basis to any local exchange carrier or intermediate switch-based carrier (or reseller of either) routing calls to a selected Carrier as a result of the bidding process described herein. Once a bill is prepared, it can be transmitted electronically (if the preparer or intended recipient wishes) by a computer associated with the preparer to a computer (or facsimile equipment) associated with the recipient or to an Internet website or database server from which the bill can be accessed and/or downloaded by the recipient. Provision can be made for the recipient of a bill to make payment electronically (using, for example, a credit card, debit card, prepaid account, or other payment arrangement) via such website or database server directly to each of the selected Carriers who provided billed telecommunications service to the bill recipient during the applicable billing cycle. As an alternative, the bill recipient could make payment electronically via such website or database server to the bill preparer, who would then process such payment, sorting the portion of such payment payable to each Carrier who provided telecommunication service to the billed recipient during the applicable billing cycle, and delivering those funds (for example, using electronic funds transfer means) to the respective Carriers. Applicable parts of each bill can also be transmitted by a computer associated with the bill preparer to a computer associated with each of the respective Carriers or to an Internet website or database server from which such parts of a bill can be accessed and/or downloaded by the respective Carrier.

Figure 11:
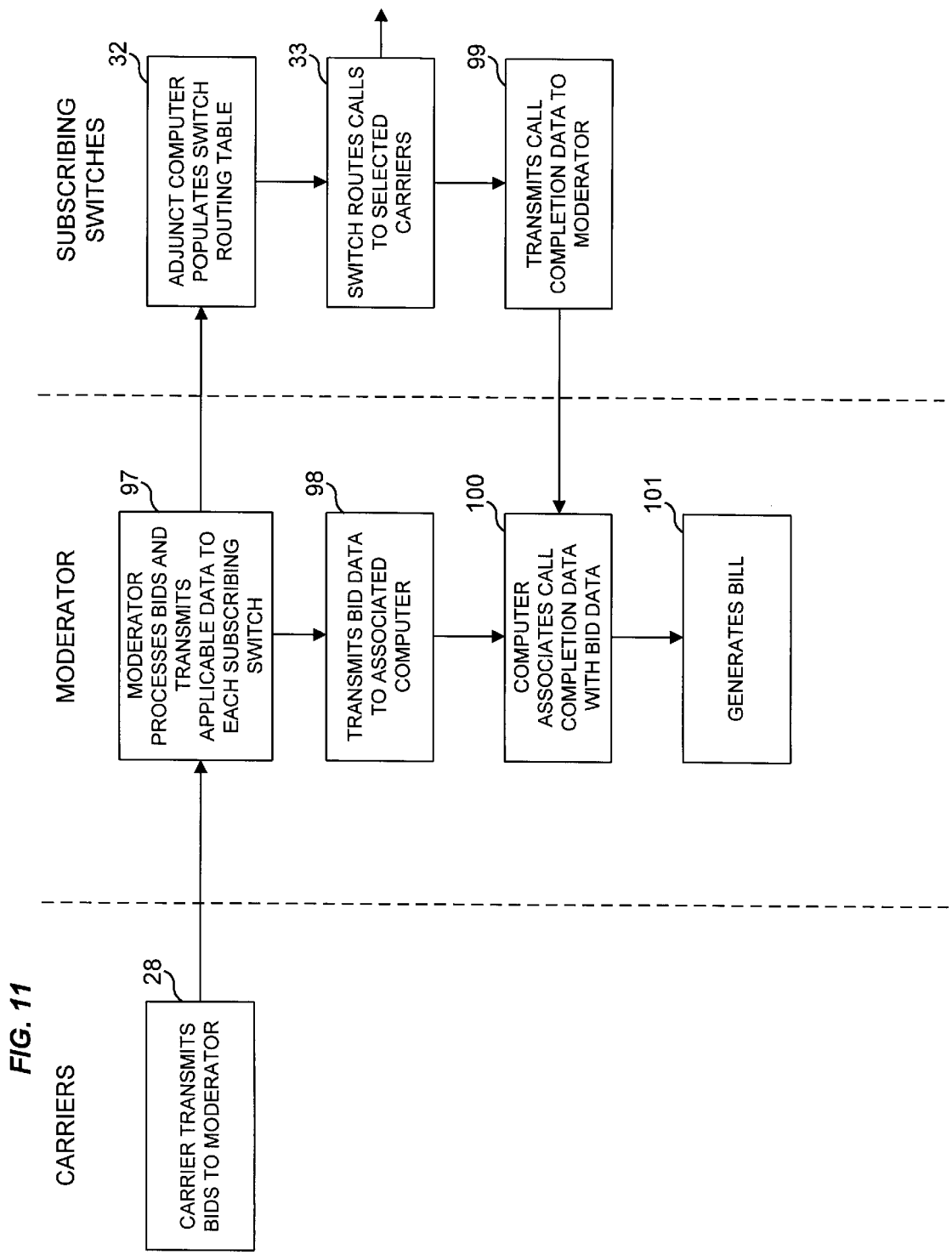
FIG. 11 is a schematic representation of an exemplary process of the invention in which a subscribing switch transmits call completion data to the Moderator to permit the Moderator to generate a bill.

In the billing arrangement illustrated in FIG. 11, in which the Moderator (or an associated computer) prepares the bill, the bidding and routing takes place as illustrated in FIG. 5 or FIG. 8. After the subscribing switch routes a call 33, the switch (or an associated computer) transmits 99 the call completion data identifying the call source, the Carrier, the applicable route or route segment data, and any other information necessary for billing purposes (e.g., the time and duration of the call) to a computer associated with the Moderator. The Moderator transmits 98 economic incentive data to this computer. The computer associates 100 the call completion information with the economic incentive data to form a billing record of each call, which is stored in a billing data base. Periodically (e.g., at the end of each billing period), this computer sorts the billing records by call source identifier (and, perhaps, by Carrier identifier) and generates a bill 101.

Figure 18:
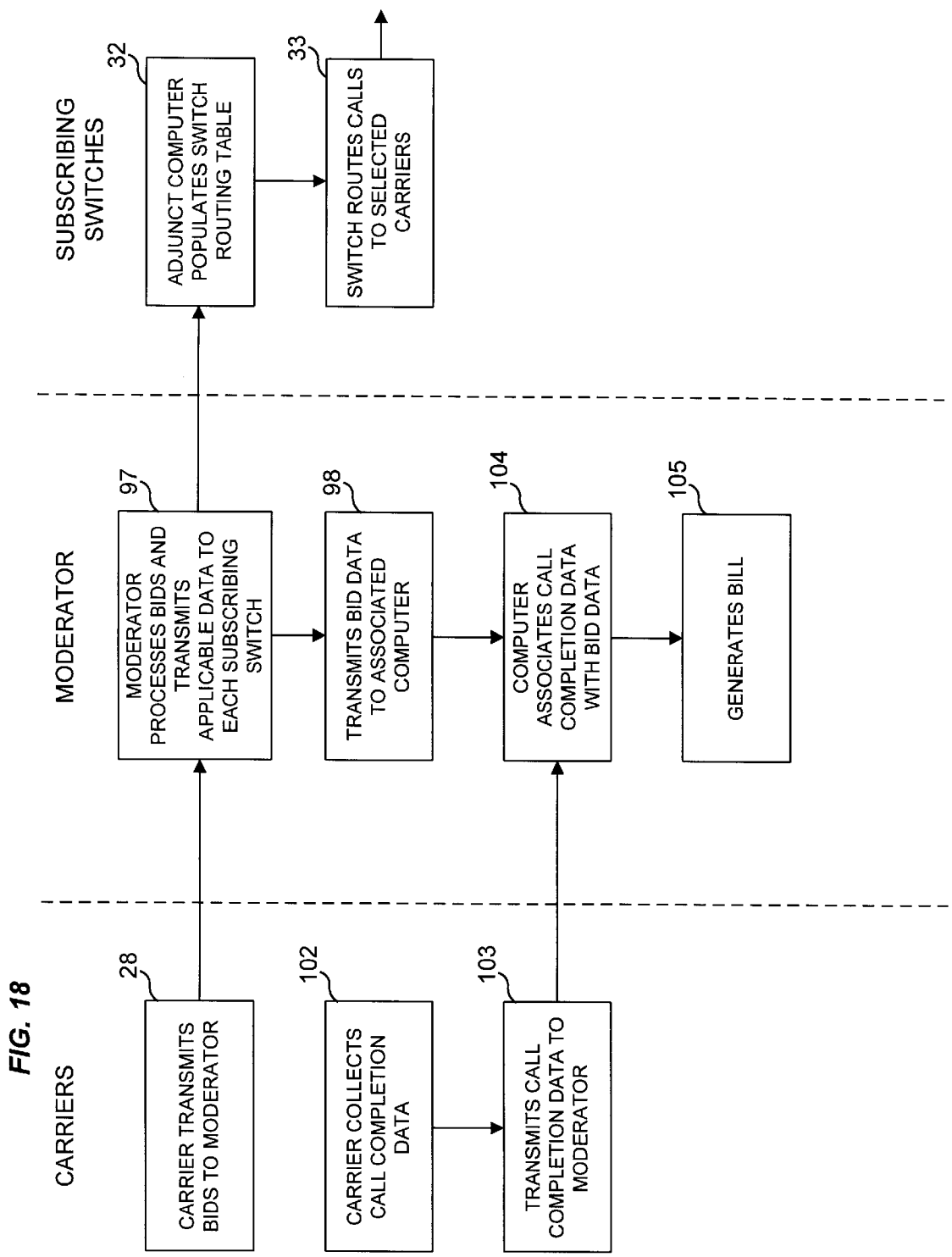
FIG. 18 is a schematic representation of an exemplary process of the invention in which a Carrier transmits call completion data to the Moderator in order for the Moderator to generate a bill.

Some participating Carriers may prefer to rely on their own switches, rather than a subscribing switch, to collect call completion data for calls routed to them by the subscribing switch. In that event, as illustrated in FIG. 18, such a Carrier's applicable switches (i.e., those handling calls routed to the Carrier by one or more subscribing switches) collect 102 the call completion data for each call and these switches (or a computer associated with those switches or their related billing or operations support systems) transmit 103 such call completion data to a computer associated with the Moderator. The Moderator transmits 98 economic incentive data to this computer. The computer associates 104 the call completion data with the economic incentive data to form a billing record of each call, which is stored in a billing data base. Periodically, this computer sorts the billing records by call source identifier (and, perhaps, by Carrier identifier) and generates a bill 105.

Once a call attempt reaches a Carrier's network, call completion data may be collected by the first switch to which the call attempt is presented or at any of several other points or elements in that Carrier's telecommunication network. For purposes of referring herein to a Carrier's collection and/or transmission of call completion data, a Carrier's switch should be considered representative of all of the Carrier's network elements capable of collecting and/or transmitting such data. With respect to facilities-based resellers using the bidding mechanism to purchase transport service on a wholesale basis from Carriers, call completion data may be collected by the subscribing switch or at other points or elements of that reseller's network. For purposes of referring herein to a reseller's collection and/or transmission of call completion data, a subscribing switch should be considered representative of all of the reseller's network elements capable of collecting and/or transmitting such data.

Figure 19:
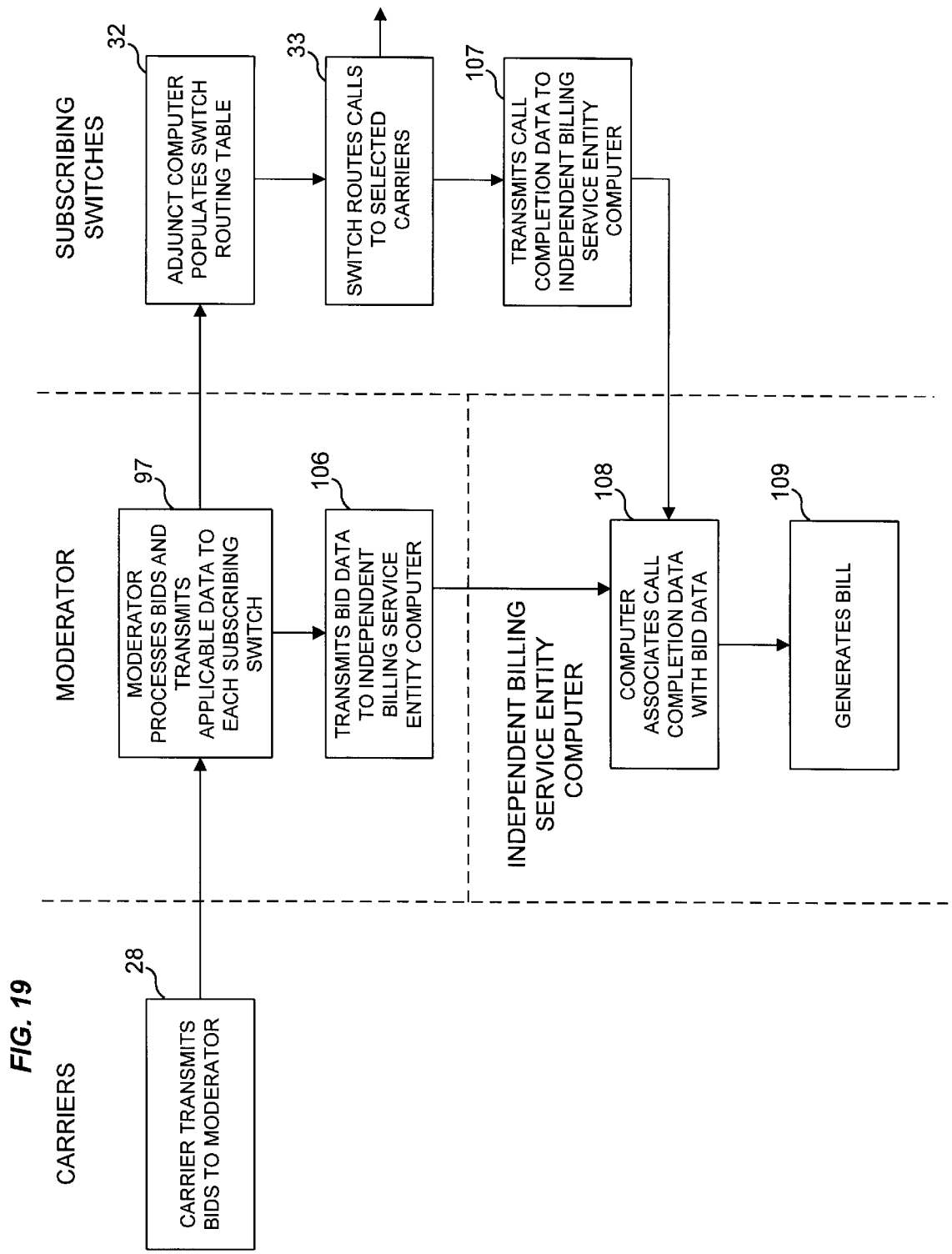
FIG. 19 is a schematic representation of an exemplary process of the invention in which a subscribing switch transmits call completion data to an independent billing service entity in order for that entity to generate a bill.
Figure 20:
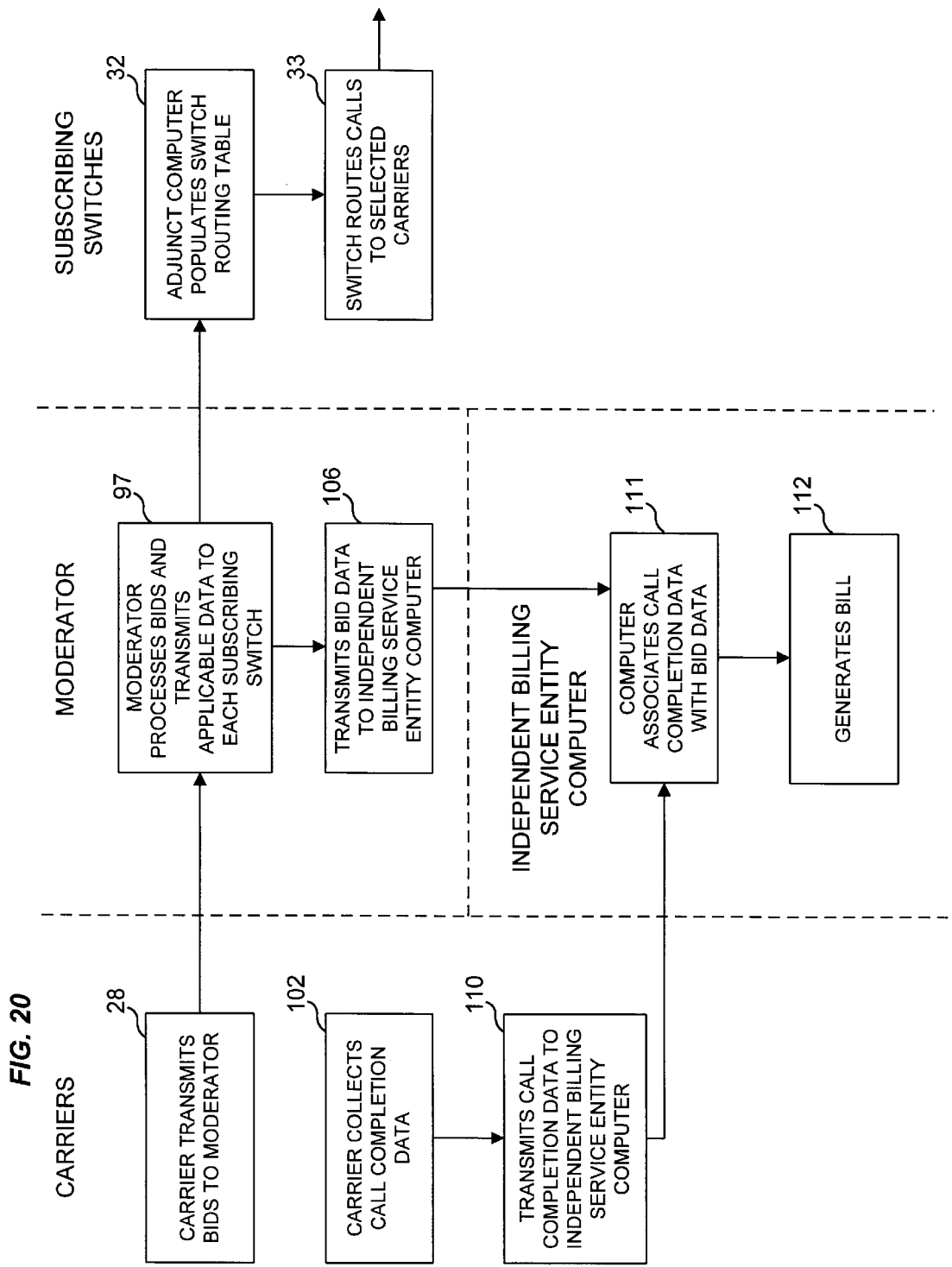
FIG. 20 is a schematic representation of an exemplary process of the invention in which a Carrier transmits call completion data to an independent billing service entity in order for that entity to generate a bill.

A central billing arrangement can also be accomplished using a billing service entity independent of the Moderator, the owner or operator of the subscribing switch (routing calls to selected Carriers), or the selected Carriers. In that case, as illustrated in FIG. 19, the subscribing switch (or an associated computer) transmits 107 the call completion data to a computer associated with the independent billing service entity. If the selected Carriers prefer to rely on their own switches, rather than a subscribing switch, to collect call completion data, as illustrated in FIG. 20, such a Carrier's applicable switches (those handling calls routed to the Carrier by a subscribing switch) collect 102 the call completion data for each call and those Carrier switches (or a computer associated with those switches or their related billing or operations support systems) transmit 110 such call completion data to a computer associated with the independent billing service entity. In either case (i.e., whether call completion data is collected and transmitted to the independent billing service entity by the subscribing switch as illustrated in FIG. 19 or by the Carriers as illustrated in FIG. 20), the Moderator (or an associated computer) transmits 106 economic incentive data to the computer associated with the independent billing service entity. This computer associates the call completion data with the economic incentive data to form a billing record of each call, which is stored in a billing data base. Periodically, the independent billing service entity sorts the billing records by call source identifier (and, perhaps, by Carrier identifier) and generates a bill.

Figure 21:
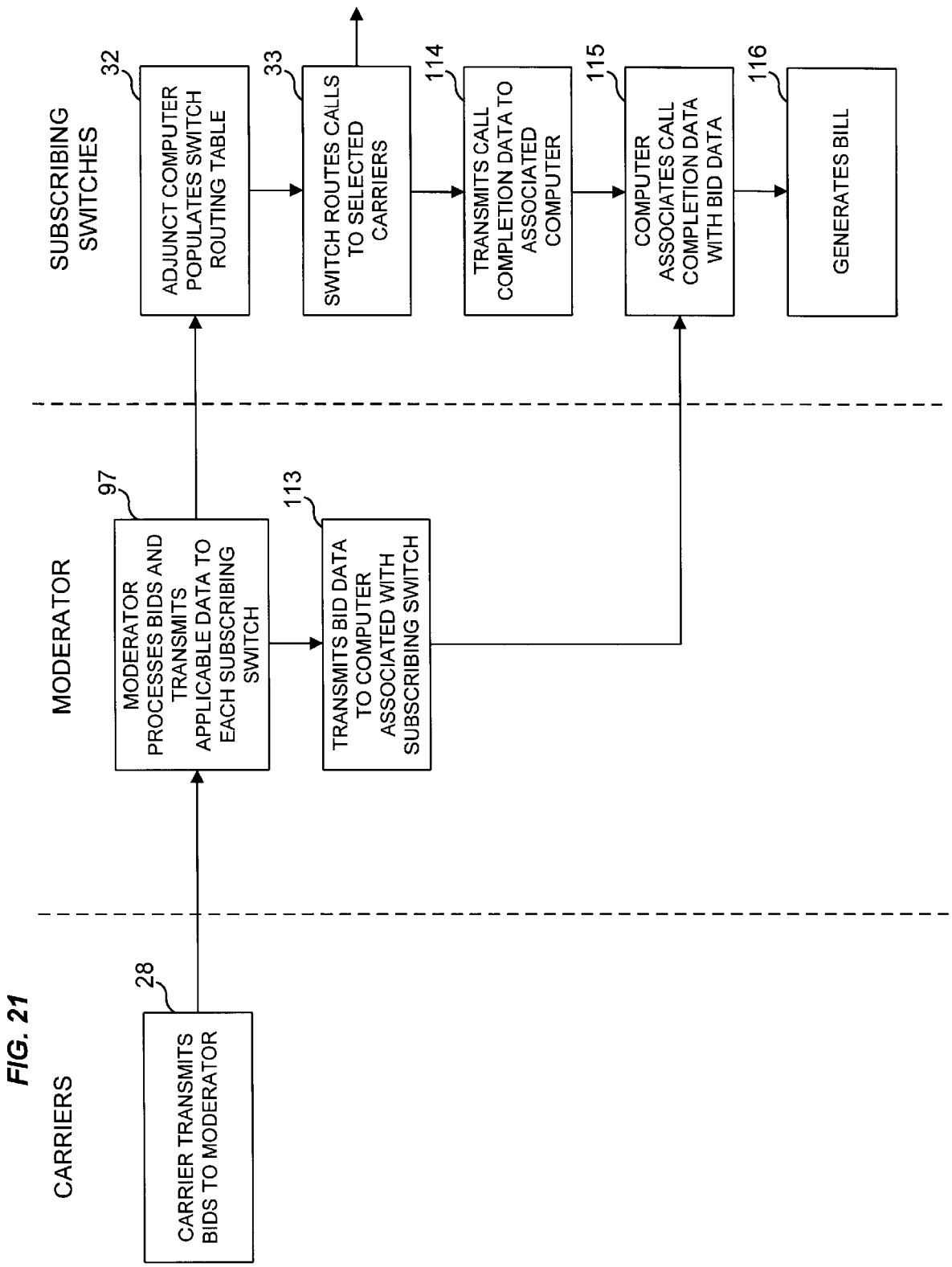
FIG. 21 is a schematic representation of an exemplary process of the invention in which a computer associated with a subscribing switch generates a bill using call completion data received from the subscribing switch.

As an alternative to the Moderator or an independent billing service entity preparing bills, the owner or operator of one or more subscribing switches (for example, a reseller of long distance service who is using the bidding mechanism to purchase such service on a wholesale basis from the Carriers) can generate bills, as illustrated in FIG. 21, by having a computer associated with one or more of its subscribing switches receive economic incentive data transmitted 113 from the Moderator (or an associated computer) and call completion data transmitted 114 from such subscribing switches. The computer receiving such data associates 115 the economic incentive data with the call completion information to form a billing record of each call, which is stored in a billing data base. Periodically, this computer sorts the billing records by call source identifier (and, perhaps, by Carrier identifier) and generates a bill 116.

Figure 22:
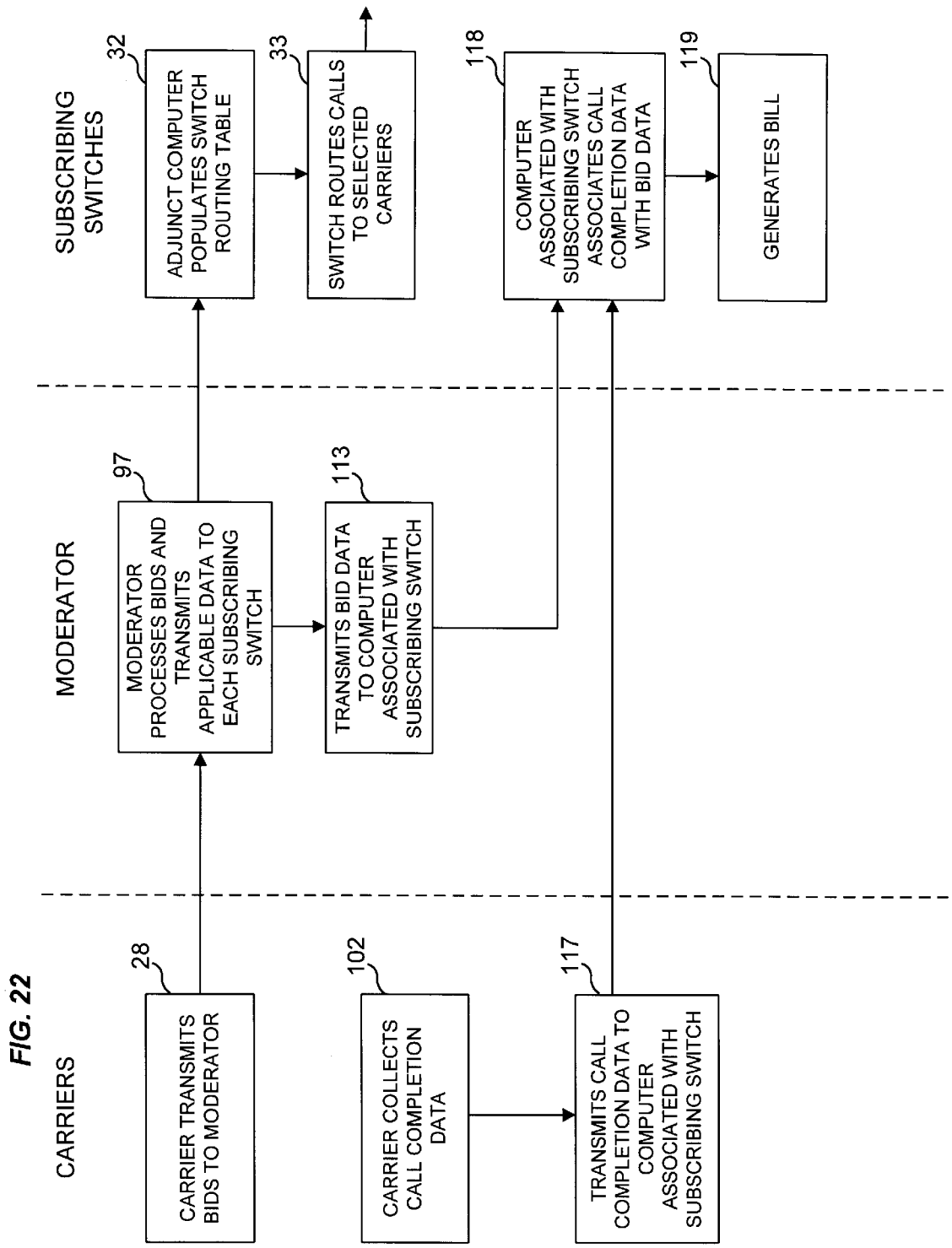
FIG. 22 is a schematic representation of an exemplary process of the invention in which a computer associated with a subscribing switch generates a bill using call completion data received from a Carrier.

Some selected Carriers may prefer to rely on their own switches, rather than a subscribing switch, to collect call completion data, but are otherwise willing to let the owner or operator of the subscribing switch prepare the bill. In that event, as illustrated in FIG. 22, such a Carrier's applicable switches (those handling calls routed to the Carrier by one or more subscribing switches) collect 102 the call completion data for each call and those Carrier switches (or a computer associated with those switches or their related billing or operations support systems) transmit 117 such call completion data to a computer associated with the subscribing switch and owned or operated by the owner or operator of the subscribing switch (or by an independent billing service entity acting on its behalf). The Moderator (or an associated computer) transmits 113 economic incentive data to the computer associated with the subscribing switch. This computer associates 118 the call completion data with the economic incentive data to form a billing record of each call, which is stored in a billing data base. Periodically, the Moderator sorts the billing records by call source identifier (and, perhaps, by Carrier identifier) and generates a bill 119.

To provide each participating Carrier and/or end user or reseller with reliable billing reconciliation information, the party generating the bills (for example, the Moderator, an independent billing service entity, or a reseller) can create a billing data report by sorting the billing records of each end user or reseller by Carrier. Periodically, the party generating the bills can create these billing data reports and transmit them to the billing or operations support systems of the respective Carrier or applicable reseller, or to the electronic address of the respective Carrier, end user or reseller.

Figure 23:
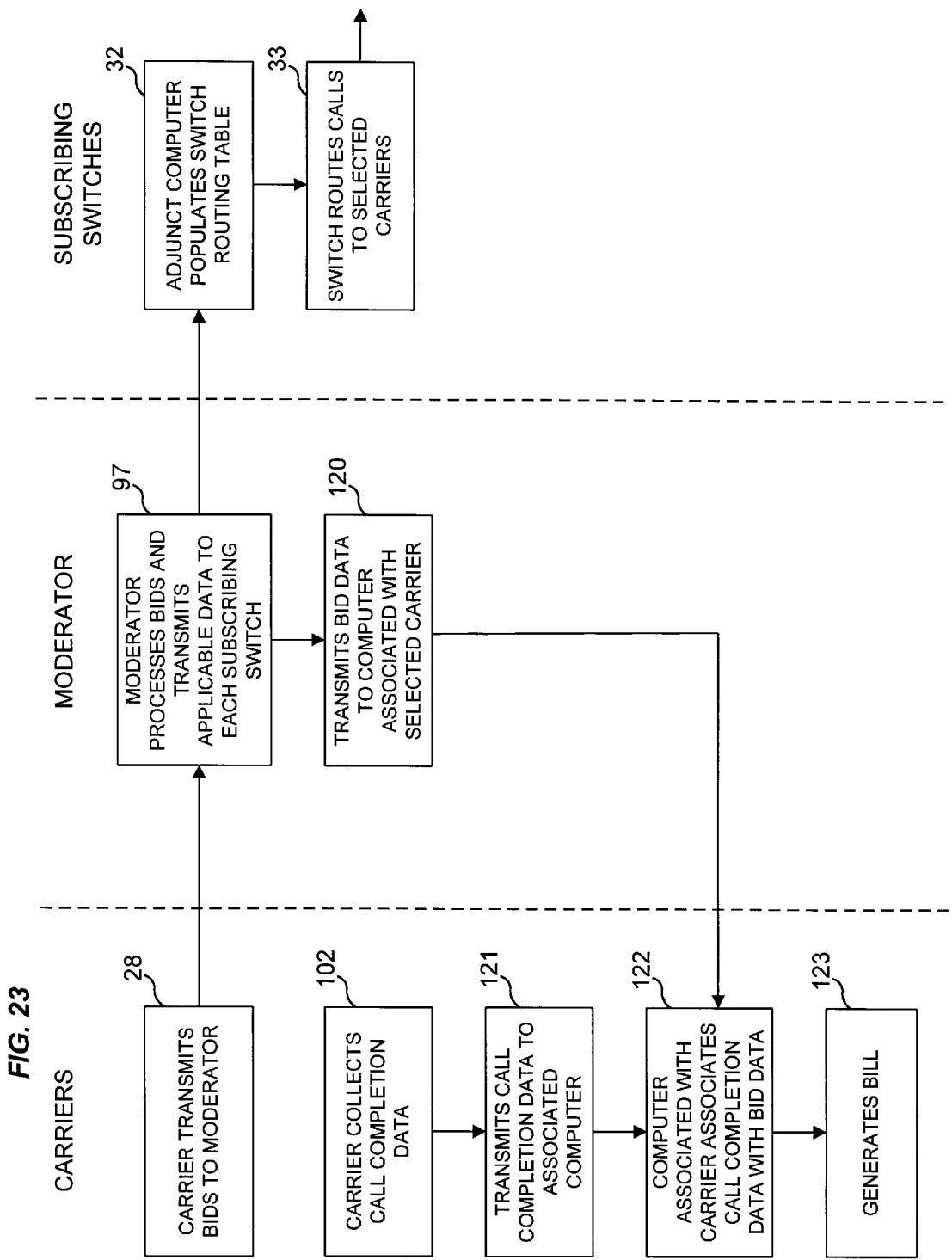
FIG. 23 is a schematic representation of an exemplary process of the invention in which a computer associated with a Carrier generates a bill using call completion data received from the Carrier.
Figure 24:
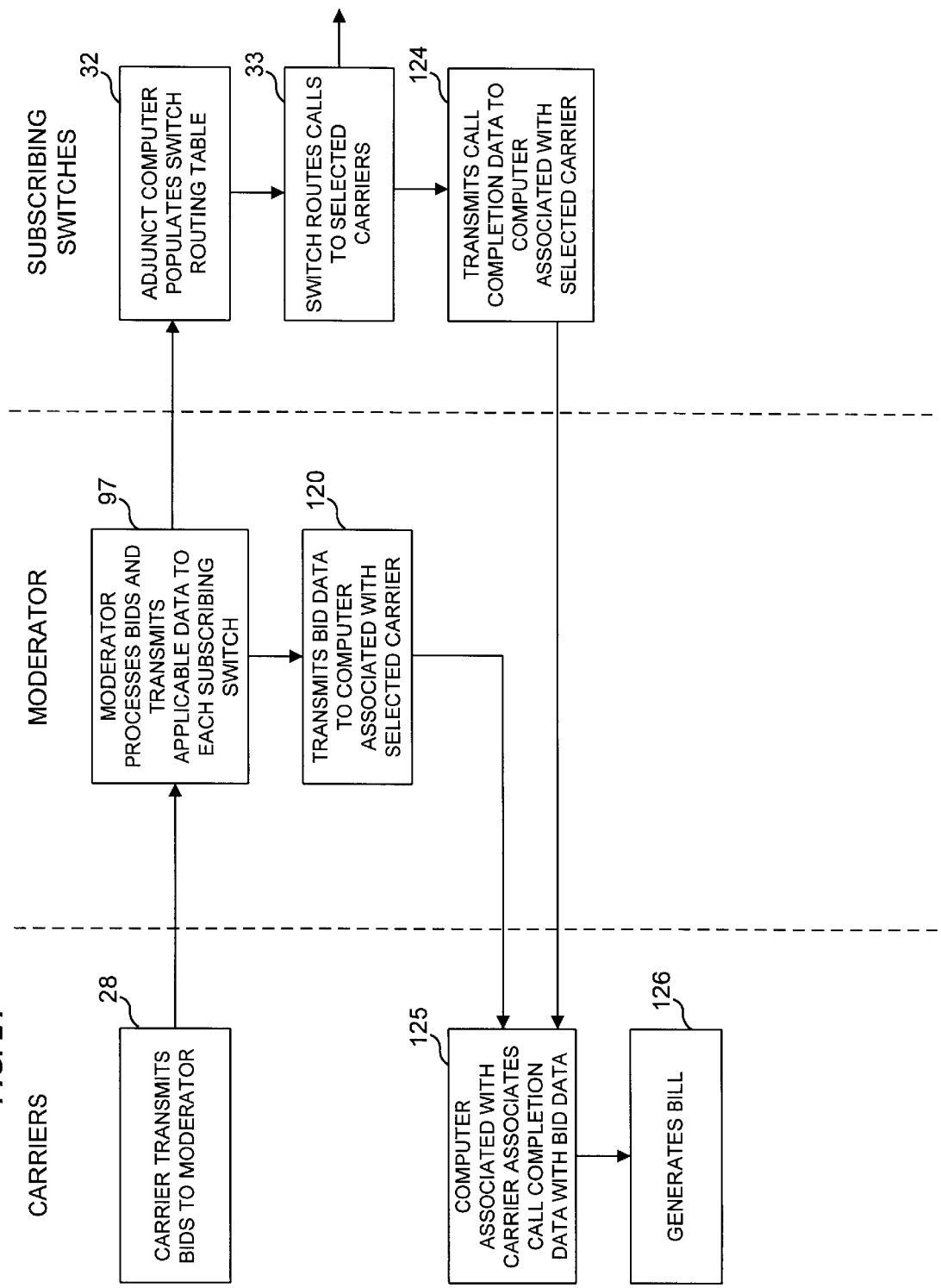
FIG. 24 is a schematic representation of an exemplary process of the invention in which a computer associated with a Carrier generates a bill using call completion data received from a subscribing switch.

In those instances where a Carrier does not wish to have a bill prepared by the Moderator or the owner or operator of a subscribing switch (e.g., an end user or reseller), the Carrier can prepare its own bill. In this case, as illustrated in FIG. 23, the Carrier's applicable switches (those handling calls routed to the Carrier by one or more subscribing switches) collect 102 the call completion data for each call and transmit 121 such call completion data, and the Moderator (or an associated computer) transmits 120 the economic incentive data, to the Carrier's billing or operations support system related to such applicable switches (or to a computer associated with such system or switches). This receiving system or computer associates 122 the call completion data with the economic incentive data to form a billing record of each call, which is stored in a billing data base. Periodically, the Carrier sorts the billing records by call source identifier and generates a bill 123. If, instead of using its own call completion data, the Carrier prefers for any reason to prepare the bill using the call completion data collected by the subscribing switch (that routed the call to the Carrier), the Carrier can elect to have the subscribing switch (or an associated computer) transmit the call completion data, as illustrated in FIG. 24, to a computer associated with the Carrier's billing or operations support systems applicable to those of its switches to which the subscribing switch routed calls.

In each of the billing arrangements described herein, the Moderator (or a computer associated with the Moderator) transmits economic incentive data to a computer which also receives call completion data from a subscribing switch or a selected Carrier, in order for the computer to generate a bill. In some cases, it may be preferable for the economic incentive data to be transmitted to this bill-generating computer by a subscribing switch (or an associated computer) or by a selected Carrier (or an associated computer).

To facilitate the entry of an end user or reseller (in either case a "Buyer") into a forward delivery transaction with a Carrier (or a reseller of that Carrier's telecommunications service), the Moderator will accommodate requests for future telecommunications service (an "RFS") from a Buyer. A "forward delivery transaction" is a purchase transaction in which a Buyer and a Carrier (or a reseller of that Carrier's telecommunications service) agree on all material terms of the transaction at the time that transaction is entered into, but delivery by the Carrier of the telecommunications service purchased by the Buyer is scheduled for a future time. That future delivery may be set for any specific delivery time in the future (for example, seconds, minutes, hours, days, weeks, months or years, or any combination thereof, after the time the transaction was entered into by the parties). In the context of this application, "delivery" means the Carrier has made available to the Buyer, either via a direct or indirect interconnection of the respective telecommunications facilities of Buyer and Carrier (or the facilities of others that the Buyer or Carrier may be using to enable that delivery to occur), the telecommunications service the Buyer previously purchased from the Carrier, such purchase having occurred at the time the terms of the transaction (under which delivery is being made) were agreed to by the Buyer and the Carrier.

Figure 25:
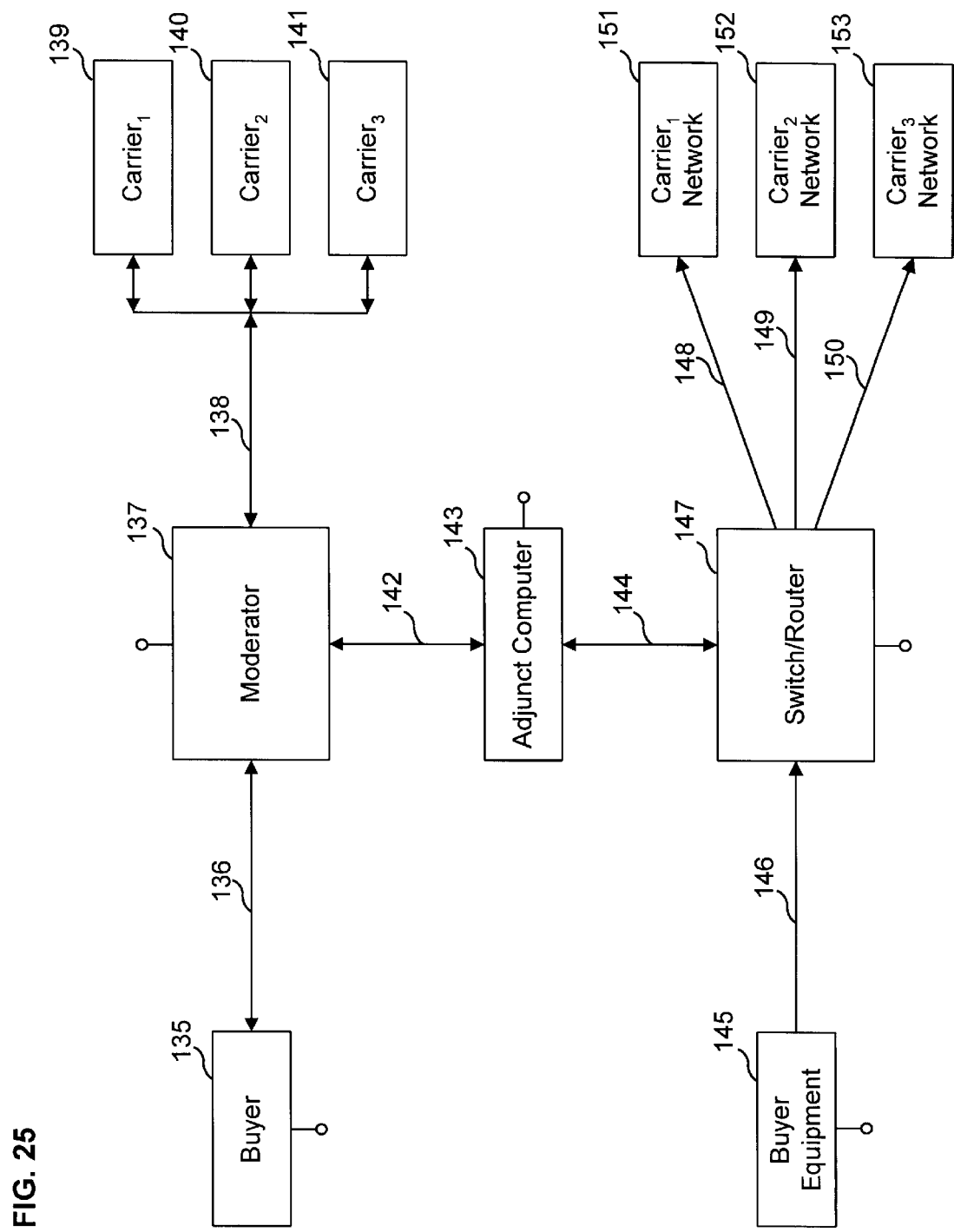
FIG. 25 is a schematic view of an exemplary system of the invention showing a shared or dedicated data link between the buyer and the Moderator, and a shared or dedicated data link between a computer adjunct to the Moderator and a Switch/Router.
Figure 26:
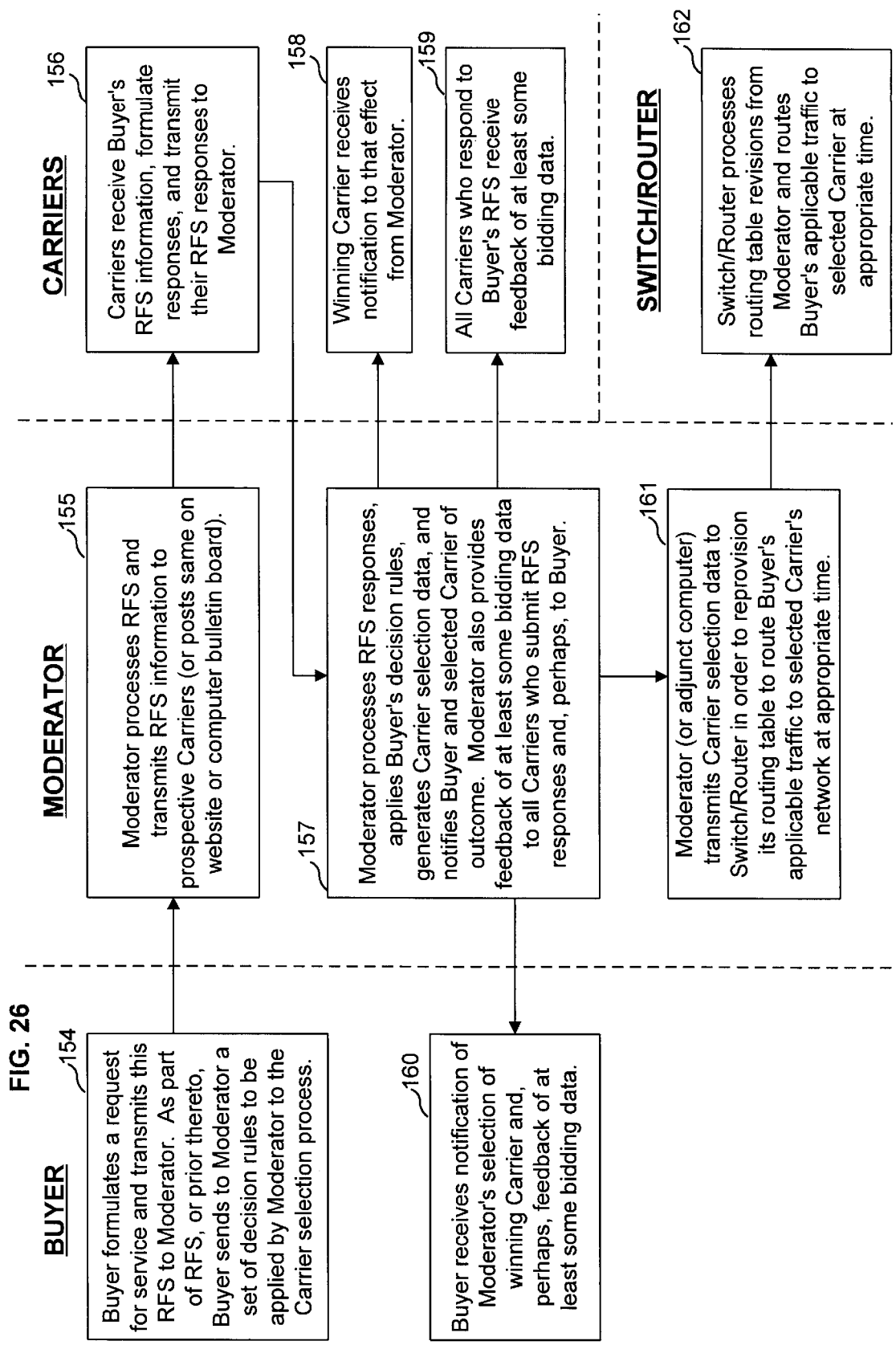
FIG. 26 is a schematic representation of an exemplary process of the invention showing transmission of buyer request information to the Moderator, transmission of Carrier responses (to such buyer requests) to the Moderator, and transmission of Carrier selection data to the applicable Switch/Router.

FIGS. 25 and 26 illustrate an exemplary system for carrying out the herein disclosed forward delivery transaction process. A Buyer formulates an RFS and the Buyer's computer 135 transmits this RFS to the Moderator 137 (perhaps by way of an adjunct computer with a data link to the Moderator) over a data link or other telecommunications facility 136. In order to provide the Moderator with sufficient information to process the RFS, the Buyer enters the information describing the RFS on a software-derived template including, for example, the originating and terminating points or addresses of the route or route segment of the traffic to be carried. This template may reside, for example, on a computer bulletin board or website maintained by Moderator (or a computer adjunct to the Moderator) and accessible to Buyer.

The software-derived template may also call for such things as: (i) the relevant future period for which service is being requested (e.g., one or more specific hours, days, weeks or months, or any combination thereof), (ii) the bandwidth capacity required (e.g., 56 kb, T-1, T-3, etc.), (iii) any minimum quality of service or priority criteria, (iv) if applicable, the number of minutes, packets, cells, frames, bytes, bits, etc. to be purchased, and/or (v) any other elements necessary to provide prospective Carriers with a precise description of the future telecommunications service the Buyer is requesting and the specific interconnection criteria and location (or locations) required by Buyer.

In many cases, the Buyer may wish to include in the RFS the maximum price it is willing to pay a Carrier for the service requested (e.g., per minute, per packet, per hour, per month, etc.). If the Buyer so specifies, the Moderator could use this maximum price as part of the selection process without necessarily disclosing it to prospective Carriers. If no Carriers submit RFS responses with prices at or below the Buyer's maximum price, the Moderator could discard all of the responses and let the Buyer decide, for example, whether it will increase the maximum price and resubmit the RFS, it will abandon the RFS process altogether, or it will wait and resubmit the RFS again later with its previous maximum price. The Buyer could also be given the opportunity by the Moderator to accept a price higher than the maximum price set by the Buyer as part of the RFS.

At any time prior to the Buyer's transmission of its RFS to the Moderator (or as part of such transmission) and/or the Moderator's processing of the RFS, the Buyer may transmit to the Moderator a set of decision rules applicable to any particular RFS (or group of RFS's) or to every RFS submitted by the Buyer—to be applied by the Moderator as part of the Carrier selection process. For example, if the Buyer wishes to limit the group of Carriers to whom it is willing to send traffic, the Buyer can communicate that preference to the Moderator, either as part of the RFS transmission or as part of a previous transmission to the Moderator. In this event the Moderator will make the RFS information available only to that group of Carriers preferred by the Buyer. Responses to the RFS from other Carriers, if any are inadvertently received, will be discarded by the Moderator.

Once the Moderator receives the Buyer's RFS, the Moderator further processes the information submitted and converts the RFS into a format that the Moderator can transmit to prospective Carriers' computers 139, 140, 141 or post on a computer bulletin board or website accessible by prospective Carriers. This distribution or posting by the Moderator may occur immediately after the RFS has been received and processed by the Moderator, or at some later time (e.g., according to a designated schedule each day). In most cases, we would expect that the Moderator would not reveal the identity of the Buyer to the prospective Carriers while the RFS is pending. Those prospective Carriers 139, 140, 141 wishing to respond to the RFS will each formulate its response, enter it (for example) on a software-derived template (which could reside in one embodiment on a computer bulletin board or website maintained by the Moderator or an adjunct computer and accessible by the Carriers) and transmit it to the Moderator 137 via data link or other shared or dedicated telecommunications facility 138.

Each Carrier may be given the opportunity to limit the list of Buyers for whom the Carrier is willing to carry traffic, and/or limit the telecommunications services the Carrier is willing to make available to any particular Buyer within one or more billing cycles (e.g., to reduce the Carrier's credit exposure to that Buyer). The Moderator can maintain each Carrier's list of approved Buyers, with or without applicable credit or capacity limits. Updates can be transmitted by each Carrier to the Moderator (or an adjunct computer) at periodic intervals. If, for any reason, the Buyer's identity is revealed in the RFS information disclosed to prospective Carriers, each Carrier can elect whether to respond to the RFS. If a Carrier were to respond to that RFS, any previous credit or capacity limitations imposed by that Carrier on that Buyer could be deemed set aside, at least for that RFS-related transaction.

The Moderator could also compare a Buyer's RFS information to data submitted to the Moderator by a prospective Carrier before this RFS was distributed or posted, assuming the Carrier had indicated, for example, its available transport capacity and the price at which it would sell service to any pre-approved Buyer. If such a Carrier's available transport capacity and pricing matched the requirements of a Buyer as specified in the Buyer's RFS, the Moderator could include this Carrier as one of the respondents to the RFS, notwithstanding the fact that the Carrier did not respond to the RFS after it was distributed or posted. As an alternative at some time in the future, if and when Carriers become more comfortable posting data on their available telecommunications service (e.g., available transport capacity) with the Moderator before an RFS is posted, the Moderator could use these pre-RFS submissions by Carriers as the primary or exclusive source of responses to the RFS.

When the Moderator distributes or posts an RFS, prospective Carriers will typically be given a deadline or cut-off time by which they must respond to the Moderator. Any responses received by the Moderator after the cut-off time will likely be discarded. From among the responses received on a timely basis, the Moderator selects the Carrier offering the best economic value to the Buyer, after applying the Buyer's decision rules, if any, and any additional determination criteria governing like transactions and known beforehand by both Buyers and Carriers (e.g., historical quality of service performance by each Carrier, sufficiency of unscheduled capacity on the Carrier's trunks connected to the routing switch, etc.).

To provide Buyers with the assurance that at least one Carrier will be available to carry their traffic at a reasonable price, the Moderator may arrange for a default Carrier to whom traffic can be routed under any of several scenarios (for example, if the prices offered by bidding Carriers rise above a ceiling price specified by the Buyer).

The Buyer can also provide the Moderator with a decision rule that directs the Moderator to select a particular Carrier, regardless of how many other Carriers respond to the Buyer's RFS or the attractiveness of the economic incentives they offer. This approach enables the Buyer to send its traffic, for example, to a specific Carrier with whom the Buyer may have an existing contract relationship pursuant to which the Buyer is committed to send that Carrier a certain volume or proportion of its traffic. This decision rule may be operative based on one or more criteria, for example, time of day, type of traffic, destination, etc. In some cases, the Buyer may specify a decision rule that a certain Carrier is to be selected unless prices offered by one or more other Carriers are substantially better (e.g., 20% lower) than that offered by the otherwise preferred Carrier. With this flexibility, the Buyer can take advantage of attractive prices and other benefits offered in the spot market without giving up the reliability and price stability offered by a term contract relationship with a primary Carrier. In FIG. 25, the Buyer's primary term contract Carrier could, if it were willing to deal with Buyer on this basis, have telecommunications facilities directly connected to Switch/Router 147, appearing as a fourth Carrier network (in addition to Carrier networks 151, 152, 153) to which the Switch/Router 147 can route a Buyer's traffic. The Moderator could then instruct the Switch/Router to route traffic to the Buyer's primary term contract Carrier as the selected Carrier when appropriate under the decision rules set by Buyer.

Once the Moderator 137 selects a Carrier to supply telecommunications service to a Buyer, the Buyer 135 and that Carrier are so notified by the Moderator via electronic transmission. In most cases this may also be the point at which the selected Carrier first learns the identity of the Buyer, unless the Buyer has given the Moderator permission to reveal the Buyer's identity to the Carriers as part of the RFS disclosure.

After the selection of the winning Carrier has been made, the Moderator 137 will transmit, to some or all of the Carriers who respond to the RFS, at least some of the bidding data submitted by responding Carriers (most likely without revealing the identity of the winning Carrier or that of the Buyer). This feedback will enable the losing Carriers to adjust their bids on the next RFS distributed to them by the Moderator.

If the Buyer and all of the prospective Carriers (within the Buyer's preferred group of Carriers) agree, or the rules under which the Moderator operates the bidding process so state and the Buyers and Carriers still decide to participate, the Moderator could provide feedback to all bidding Carriers of some or all of the prices bid by the different Carriers in response to any RFS (most likely without revealing the identity of the winning Carrier or that of the Buyer). This feedback would enable the Carriers, while the bidding for a particular RFS is in progress and before a winner is selected, to adjust their bids and submit amended responses to the Moderator.

The Moderator may also provide to the Buyer, before or after the Moderator selects the winning Carrier, at least some of the bidding data from some or all of the Carriers responding to the Buyer's RFS.

Once the Moderator has selected a winning Carrier for the Buyer's RFS, the Moderator will transmit all or a portion of the transaction information to an Adjunct Computer 143 via data link or other dedicated or shared telecommunications facility 142. This Adjunct Computer 143 further processes the transaction information in order to provision the applicable Switch/Router 147 (i.e., the switch/router at which the Buyer's traffic will be routed to the winning Carrier's network) to execute the transaction (that is, to facilitate delivery in the context of a forward delivery purchase transaction) in accordance with the bidding process.

At or before the time the relevant telecommunications traffic (e.g., a voice or data transmission) from the Buyer's Equipment 145 reaches the Switch/Router 147 via a shared or dedicated facility 146, the Adjunct Computer 143 transmits routing instructions to the appropriate routing table of the Switch/Router 147 via data link or other shared or dedicated telecommunications facility 144. This transmission of routing instructions can be initiated by a query from the Switch/Router to the Adjunct Computer or can be downloaded at periodic intervals by the Adjunct Computer to the Switch/Router. Applying these routing instructions, the Switch/Router 147 routes the Buyer's traffic to shared or dedicated transmission facilities 148, 149, 150 connected to the winning Carrier's network point-of-presence 151, 152 or 153, respectively.

All of the functions of the Adjunct Computer 143 can be performed by the Moderator 137, if use of an adjunct computer is not deemed advantageous for any reason.

The Moderator can communicate with one or more adjunct computers, which each can communicate with one or more Switch/Routers. In the alternative, the Moderator can communicate directly with one or more Switch/Routers via a data link or other shared or dedicated telecommunications facility.

Different types of telecommunications transmissions (e.g., voice, data, video, or subclasses or priority categories of any of these) from the telecommunication equipment of a single Buyer or of many Buyers may be routed by the Switch/Router 147 to the networks of different Carriers. The term "call attempt" is meant to include all types of calls or transmissions over all kinds of wired and wireless telecommunications networks (e.g., circuit-switched, packet data, asynchronous transfer mode, frame relay, etc.). The term "Carrier" includes any seller or reseller of telecommunications service, regardless of whether that seller or reseller owns or operates any telecommunications equipment or facilities.

References herein to "data links" or other shared or dedicated telecommunications facilities may, for example, include any wireline or wireless facilities, whether part of the public switched telephone network, private lines, the Internet, fiber optic facilities, coaxial cable, electric utility power lines, Ethernet or other local area network (LAN), metropolitan area network (MAN) or wide area network (WAN) connections.

Some Buyers may elect to submit an RFS that includes more than one request for future telecommunications services, e.g., one RFS specifying several routes or route segments, each with the same or different (i) originating and terminating points or addresses of each route or route segment, (ii) future periods for which service is being requested, (iii) bandwidth capacity required, (iv) quality of service or priority criteria, and/or (v) number, if applicable, of minutes, packets, cells, frames, bytes, bits, etc. to be purchased. This composite RFS may also be submitted, for example, for the same route and/or route segment, but for different future periods. The Buyer may specify a maximum price it is willing to pay a Carrier for the composite of all of the telecommunications services it requests in the RFS, or it may specify separate maximum prices for each (or any other combination) of the elements or telecommunications services included in this RFS. Once the Moderator has selected a winning Carrier for the Buyer's RFS, the Moderator will transmit (perhaps by way of one or more adjunct computers with data links to the appropriate Switch/Routers) routing instructions to the one or more Switch/Routers at which the Buyer's traffic will be routed to the selected Carrier's network.

To facilitate billing activity, the Switch/Router 147 could transmit detailed information concerning each transmission by the Buyer (e.g., call detail reports, packet counts, byte volumes, etc.) to a Billing Computer immediately or at intervals specified by the respective administrator of the Moderator, the Switch/Router or the Billing Computer, or by the Buyer or the selected Carrier. This data, or billing reports derived therefrom, could thereafter be transmitted by the Billing Computer to the Buyer and/or the winning Carrier via data link or other telecommunications facility. The functions of the Billing Computer could, as an alternative, be performed by the Moderator. In that event, the applicable Switch/Routers would send detailed information on each transmission by a Buyer to the Moderator. If billing for the particular purchase transaction entered into by the Buyer and the Carrier does not require such detailed information (e.g., the Buyer purchased a set amount of bandwidth capacity for a certain future period, without regard to how many packets or bytes are actually transmitted), the Moderator could facilitate billing activity at any time (before or after the future delivery date specified as part of the transaction) and without receiving detailed information from the Switch/Router. In this case, the Moderator would likely have all the relevant billing data as soon as the Buyer and Carrier entered into this forward delivery purchase transaction.

In addition, any of the billing variations described in our Continuation-in-Part Application entitled "Bidding for Telecommunications Traffic and Billing for Service," filed May 17, 1999 with the U.S. Pat. (application Ser. No. 09/313,114, incorporated herein by reference) could be implemented, with the above-described Switch/Router considered the subscribing switch in such Application.

Figure 27:
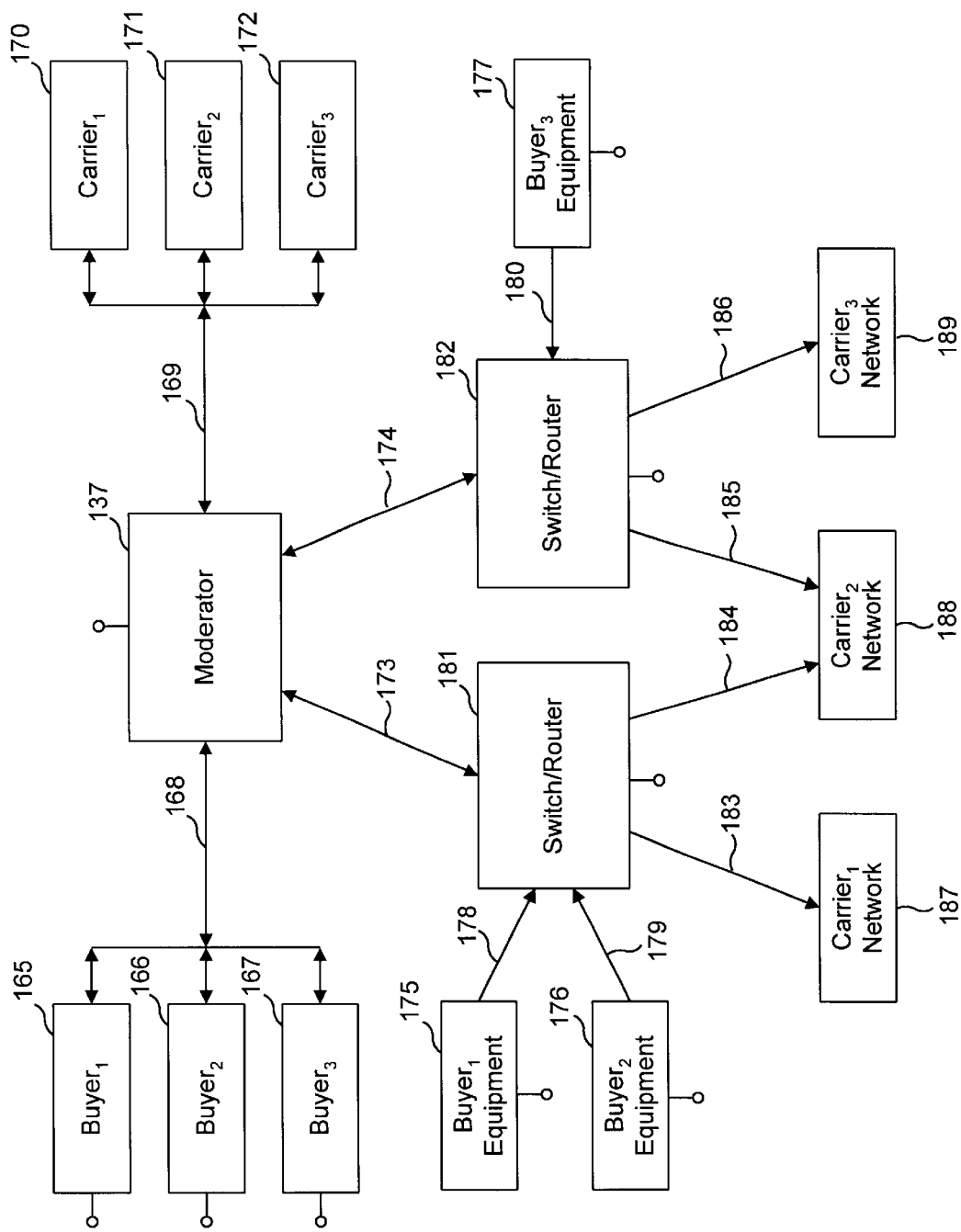
FIG. 27 is a schematic view of an exemplary system of the invention showing a shared data link between the buyer and the Moderator, and shared or dedicated data links between the Moderator and each of two Switch/Routers, with two buyers' equipment sending telecommunications traffic to the same Switch/Router.

FIG. 27 illustrates a schematic view in which the Moderator 137 transmits routing instructions to more than one Switch/Router. Switch/Router 181 routes traffic from Buyers 175, 176 to Carrier networks 187, 188, and Switch/Router 182 routes traffic from Buyer 177 to Carrier networks 188, 189. In FIG. 27, the Moderator performs the functions of the Adjunct Computer 143 in FIG. 25. As an alternative to the architecture illustrated in FIG. 27, one or more adjunct computers could be inserted between the Moderator 137 and one or more of the Switch/Routers 181, 182. Such adjunct computers could perform the functions of the Adjunct Computer 143 in FIG. 25 as described above. Billing can be accomplished using any of the variations described above in reference to FIG. 25.

What is claimed is:

1. A method for routing a telecommunication call attempt presented by a Buyer of telecommunication service to a telecommunication switch, associated with a switching point on a telecommunications network, to a first telecommunication Carrier of a plurality of telecommunication Carriers in accordance with economic incentives arrived at through a bidding process involving a central processor, referred to as a Moderator, comprising the steps of:

a. in the Buyer, formulating a request for telecommunication service over at least one route or route segment on at least one telecommunication network during at least one specific future time interval and transmitting such request to the Moderator;

b. in the Moderator, processing such request and distributing a processed request to a plurality of telecommunication Carriers;

c. in each Carrier, receiving the processed request, formulating a response to the processed request and transmitting such response, including economic incentive data, to the Moderator;

d. in the Moderator, receiving the response from each Carrier, entering the economic incentive data from each Carrier in the Moderator's database, and processing the economic incentive data to generate Carrier selection data;

e. in the Moderator, transmitting at least a portion of the economic incentive data contained in the plurality of responses received by the Moderator to at least a portion of the plurality of telecommunication Carriers;

f. in the Moderator, transmitting to the switch, the carrier selection data associated with such telecommunication service over the route or route segment on at least one telecommunication network;

g. in the switch, entering the carrier selection data into the switch's database; and h. in the switch, routing the call attempt to the first telecommunication Carrier in accordance with the carrier selection data.

2. A method of claim 1 including transmitting at least a portion of the carrier selection data to the first telecommunication Carrier.

3. A method of claim 1 including transmitting at least a portion of the carrier selection data to the Buyer.

4. A method of claim 1 comprising, in the Moderator, receiving decision rides from the Buyer and processing the economic incentive data and the decision rules to generate carrier selection data.

5. A method of claim 1 in which the Buyer transmits the request to the Moderator by entering request data into a first software defined template.

6. A method of claim 5 in which the first software defined template resides on a computer bulletin board maintained by the Moderator.

7. A method of claim 5 in which the first software defined template resides on a web site maintained by the Moderator.

8. A method of claim 5 in which the request data comprises a plurality of the following elements: the route or route segment's end points; the specific future time interval; required transport capacity; required quality of service criteria; a set of acceptable Carriers; and the maximum acceptable price.

9. A method of claim 1 in which the Moderator distributes the processed requests to the Carriers by posting the processed request on a computer bulletin board maintained by the Moderator and accessible to the Carriers.

10. A method of claim 1 in which the Moderator distributes the processed requests to the Carriers by posting the processed requests at a website maintained by the Moderator and accessible to the Carriers.

11. A method of claim 1 in which the first Carrier responds to the request by entering response data into a second software defined template.

12. A method of claim 1 in which the first Carrier transmits a list of approved Buyers to the Moderator.

13. A method of claim 1 in which the first Carrier transmits to the Moderator a pre-request submission, including response criteria, for use by the Moderator as the Carrier's response to any request meeting the response criteria.

14. A method of claim 1 in which the carrier selection data corresponds to a default Carrier.

15. A method of claim 1 in which the carrier selection data is transmitted to the first switch by means of a transmission and processing medium comprising an adjunct computer.

16. A method of claim 1 in which the carrier selection data is transmitted to the switch periodically.

17. A method of claim 1 in which the carrier selection data is transmitted to the switch in response to a query from the switch.

18. A method of claim 1 in which the Moderator transmits at least a portion of the economic incentive data to at least a portion of the plurality of Carriers subsequent to generating carrier selection data.

19. A method of claim 1 comprising, in the Moderator, receiving a set of decision riles from the Buyer and processing the request, together with the set of decision rules, to formulate a processed request.

20. A method for routing a telecommunication call attempt presented by a Buyer of telecommunication service to a telecommunication switch, associated with a switching point on a telecommunications network, to a first telecommunication Carrier of a plurality of telecommunication Carriers in accordance with economic incentives arrived at through a bidding process involving a central processor, referred to as a Moderator, comprising the steps of, in the Moderator:
   a) receiving from the Buyer, a request for telecommunication service over at least one route or route segment on at least one telecommunications network during at least one specific future time interval;
   b) processing the request and distributing the processed request to a plurality of Carriers;
   c) receiving a response including the economic incentive data from at least the first telecommunication Carrier;
   d) transmitting at least a portion of the economic incentive data to at least a portion of the plurality of Carriers;
   e) entering the economic incentive data received from the first telecommunication Carrier in a database and processing the economic incentive data, to generate carrier selection data; and
   f) transmitting the carrier selection data to the switch for entry into the switch's data base for use in routing the call attempt to the first telecommunication Carrier.

21. A method of claim 20 including transmitting at least a portion of the carrier selection data to the Buyer.

22. A method of claim 20 including transmitting at least a portion of the carrier selection data to the first telecommunication Carrier.

23. A method of claim 20 in which the Moderator maintains a computer bulletin board comprising a first software defined template in which the Buyer enters request data.

24. A method of claim 20 in which the Moderator maintains a website comprising a first software defined template in which the Buyer enters request data.

25. A method of claim 20 in which the request data comprises a plurality of the following elements: the route or route segment's end points; the specific future time interval; the required transport capacity; required quality of service criteria, a set of acceptable Carriers; and the maximum acceptable price.

26. A method of claim 20 in which the Moderator distributes the processed requests to the Carriers by posting the processed requests on a computer bulletin board maintained by the Moderator and accessible to the Carriers.

27. A method of claim 20 in which the Moderator distributes the processed requests to the Carriers by posting the processed requests on a website maintained by the Moderator and accessible to the Carriers.

28. A method of claim 20 in which the Moderator receives response data from the first telecommunication Carrier by means of a second software defined template.

29. A method of claim 20 in which the Moderator receives a list of approved Buyers from the first telecommunication Carrier.

30. A method of claim 20 in which the Moderator receives decision rules from the Buyer and processes the economic incentive data and the decision rules to generate carrier selection data.

31. A method of claim 20 in which the Moderator receives from the first Carrier, a pre-request submission, including response criteria, for use by the Moderator as the Carrier's response to any request meeting the response criteria.

32. A method of claim 20 in which the Moderator transmits carrier selection data corresponding to a default Carrier.

33. A method of claim 20 in which the carrier selection data is transmitted to the first switch by means of a transmission and processing medium comprising an adjunct computer.

34. A method of claim 20 in which the carrier selection data is transmitted to the switch periodically.

35. A method of claim 20 in which the carrier selection data is transmitted to the switch in response to a query from the switch.

36. A method of claim 20 in which the Moderator transmits at least a portion of the economic incentive data to at least a portion of the plurality of Carriers subsequent to generating carrier selection data.

37. A method of claim 20 comprising receiving a set of decision rules from the Buyer and processing the request together with the set of decision rules, to formulate a processed request.

38. A method of claim 20 including generating billing data prior to the specific future time interval and transmitting the billing data to at the Buyer and the first telecommunication Carrier.

39. A method of claim 38 in which the billing data is transmitted prior to the specific future time interval.

40. A telecommunications traffic bidding Moderator for enabling a first telecommunication switch to route a call attempt presented by a Buyer of telecommunication service to a first telecommunication Carrier in accordance with economic incentives arrived at through a bidding process, comprising:
   a. a computer with a processor and a memory;
   b. means for receiving from the Buyer, a request for telecommunication service over at least one route or route segment on at least one telecommunication network during at least one specific future time interval and storing the request in the memory;
   c. means for processing the request to formulate a processed request;
   d. means for transmitting the processed request to the plurality of telecommunication Carriers;
   e. means for receiving a response including economic incentive data relating to the request for telecommunication service, from at least the first telecommunication Carrier and storing the response in the memory;
   f. means for transmitting at least a portion of the economic incentive data to at least a portion of the plurality of telecommunication Carriers;
   g. means within the processor for generating carrier selection data based on the economic incentive data; and
   h. means for transmitting the carrier selection data to the switch for entry into the switch database for use in routing the call attempt to the first telecommunication Carrier during the specific future time interval.

41. A bidding Moderator of claim 40 including means for transmitting the carrier selection data to the first telecommunication Carrier.

42. A bidding Moderator of claim 40 including means for transmitting the carrier selection data to the Buyer.

43. A bidding Moderator of claim 40 including means for receiving decision rules from the Buyer and processing the economic incentive data and the decision rules to generate carrier selection data.

44. A bidding Moderator of claim 40 comprising a computer bulletin board accessible by the Buyer, provided with a first software defined template, for entry of request data by the Buyer.

45. A bidding Moderator of claim 40 comprising a website provided with a first software defined template for entry of request data by the Buyer.

46. A bidding Moderator of claim 40 including means for receiving request data comprising a plurality of the following elements: the route or route segment's end points; the specific future time interval; the required transport capacity; required quality of service criteria; a set of acceptable Carriers; and the maximum acceptable price.

47. A bidding Moderator of claim 40 comprising a computer bulletin board accessible by the Carriers for posting processed requests.

48. A bidding Moderator of claim 40 comprising a website accessible by the Carriers for posting processed requests.

49. A bidding Moderator of claim 40 provided with a second software defined template for receiving response data from the first Carrier.

50. A bidding Moderator of claim 40 comprising an adjunct computer equipped to handle a portion of the Moderator's processing and communication functions.

51. A bidding Moderator of claim 40 including means for receiving a set of decision rules from the Buyer and processing the request, together with the set of decision rules, to formulate a processed request.

52. A bidding Moderator of claim 40 including means for transmitting at least a portion of the economic incentive data to at least a portion of the plurality of Carriers subsequent to generating carrier selection data.

53. A bidding Moderator of claim 40 including means for receiving from the switch a query requesting the carrier selection data.

54. A method for billing a Buyer of telecommunication service for call attempts presented to a telecommunication switch, associated with a switching point on a telecommunications network, routed to a first telecommunication Carrier of a plurality of telecommunication Carriers in accordance with economic incentives arrived at through a bidding process involving a central processor, referred to as a Moderator, comprising the steps of:

a. in the Buyer, formulating a request for telecommunication service over at least one route or route segment on at least one telecommunication network during at least one specific future time interval and transmitting such request to the Moderator;

b. in the Moderator, processing such request and distributing a processed request to a plurality of telecommunication Carriers;

c. in at least the first telecommunication Carrier, receiving the processed request, formulating a response to the processed request and transmitting such response, including economic incentive data, to the Moderator;

d. in the Moderator, receiving the response from at least the first telecommunication Carrier, entering the economic incentive data from at least the first telecommunication Carrier in the Moderator's database, and processing the economic incentive data to generate carrier selection data;

e. in the Moderator, transmitting at least a portion of the economic incentive data contained in the responses received by the Moderator, to at least a portion of the plurality of telecommunication Carriers; and f. in the Moderator, generating billing data and transmitting the billing data to the Buyer and the first telecommunication Carrier.

55. A method of claim 54 in which the billing data is transmitted prior to the specific future time interval.

* * * * *

UNITED STATES PATENT AND TRADEMARK OFFICE
CERTIFICATE OF CORRECTION

PATENT NO. : 6,269,157 B1  Page 1 of 1
DATED : July 31, 2001
INVENTOR(S) : William F. Coyle It is certified that error appears in the above-identified patent and that said Letters Patent is hereby corrected as shown below:

<u>Title page,</u>
Item [75] should read: Item [75] Inventors: Jack J. Johnson, Summit, New Jersey (US)
William F. Coyle, Summit, New Jersey (US)

Signed and Sealed this

Twenty-second Day of January, 2002

*Attest:*

JAMES E. ROGAN
*Attesting Officer*  *Director of the United States Patent and Trademark Office*